United States Patent [19]

Tyagi et al.

[11] Patent Number: 5,759,773
[45] Date of Patent: Jun. 2, 1998

[54] SENSITIVE NUCLEIC ACID SANDWICH HYBRIDIZATION ASSAY

[75] Inventors: Sanjay Tyagi, New York, N.Y.; Fred R. Kramer, Riverdale, N.Y.; Paul M. Lizardi, Privada Cerritos, Mexico; Ulf D. Landegren, Uppsala, Sweden; Herman J. Blok, AD veenendaal, Netherlands

[73] Assignee: The Public Health Research Institute of the City of New York, Inc., New York, N.Y.

[21] Appl. No.: 393,888

[22] Filed: Feb. 24, 1995

Related U.S. Application Data

[63] Continuation of Ser. No. 157,367, Nov. 23, 1993, abandoned, which is a continuation of Ser. No. 6,073, Jan. 15, 1993, abandoned.

[51] Int. Cl.$^6$ .................. C12Q 1/68; C12P 19/34; C07H 21/04
[52] U.S. Cl. .................. 435/6; 435/91.1; 435/91.2; 536/24.3; 536/24.31; 536/24.33
[58] Field of Search .................. 435/6, 91.2, 91.1; 536/24.3, 24.31, 24.33

[56] References Cited

U.S. PATENT DOCUMENTS

| | | | |
|---|---|---|---|
| 4,683,202 | 7/1987 | Mullis | 435/91 |
| 4,775,619 | 10/1988 | Ureda | 435/6 |

FOREIGN PATENT DOCUMENTS

| | | |
|---|---|---|
| 439 182 A2 | 7/1991 | European Pat. Off. |
| WO 89/09284 | 10/1989 | WIPO |
| WO 92/18521 | 10/1992 | WIPO |

OTHER PUBLICATIONS

Blok, H.J., Target–Dependent Amplifiable Nucleic Acid Hybridization Probes. 1992. Doctoral Thesis. Eindhoven University of Technology, Eindhoven, The Netherlands.
Krinke et al., "The cleavage specificity of RNase III", Nucleic Acids Res. 18(16):4809–4815, 1990.
Haseloff et al., "Simple RNA enzymes with new and highly specific endoribonuclease activities", Nature 334:585–591, Aug. 1988.
Gibco/BRL catalog, "SuperScript(tm) Choice system for cDNA synthesis", pp. 368–369, Feb. 1992.
Chu et al., Nucleic Acids Rev. V. M. N.Y. 1986, pp. 5591–5603.
Barary, Proc. Natl. Acad. Sci., V. 88, Jan. 1991, 189–93.
Matthews et al, Anal. Biochem, V. 169, 1988, 1–2 J.
Landegren et al. Science, v. 241, Aug. 1988, 1077–1080.
Korarska et al, Cell, v. 57 May 5, 1989, 423–31.

*Primary Examiner*—Stephanie W. Zitomer
*Assistant Examiner*—Jeffrey Fredman
*Attorney, Agent, or Firm*—Fish & Richardson P.C.

[57] ABSTRACT

Nucleic acid sandwich hybridization assays are provided that incorporate one or a combination of background reduction steps. Those steps include use of a separate capture probe and separation from immobilized capture probes by cleavage and isolation. A very sensitive assay for RNA targets includes both of those steps, plus RNA binary probes, an RNA-directed RNA ligase and amplification by an RNA-directed RNA polymerase. Kits of reagents for performing assays according to this invention are also provided.

6 Claims, 10 Drawing Sheets

Capture Probe 3

```
         10         20         30         40        49
5' Biotin-TACGACTGCT ACCAAGATAA CTTTTCCTTC TAAATGTGTA CAATCTAGC 3'
```

Capture Probe 4

```
         10         20         30         40        49
5' Biotin-TACGATGTCT GTTGCTATTA TGTCTACTAT TCTTTCCCCT GCACTGTAC 3'
```

Binary Probe 8

```
      10         20         30         40         50         60
5' GGGGACCCCC CCGGAAGGGG GGGACGAGGU GCGGGCACCU CGUACGGGAG UUCGACCGUG 70         80         90
   ACGCUCUAGC AGGCGGCCUU AACUGUAGUA CU 3'
```

Binary Probe 9

```
         10         20         30         40         50         60
5' GGUGAAAUUG CUGCCAUUGA GAUCUAGAGC ACGGGCUAGC GCUUUCGCGC UCUCCCAGGU 70         80         90        100        110        120
   GACGCCUCGU GAAGAGGCGC GACCUUCGUG CGUUUCGGUG ACGACGAGA ACCGCCACGC 130        140        150        160        170        180
   UGCUUCGCAG CGUGGCUCCU UCGCGCAGCC CGCUGCGCGA GGUGACCCCC CGAAGGGGGG

185
   UUCCC 3'
```

FIG. 2

Capture Probe 53

5' Biotin-GGCGACUGCU ACCAAGAUAA CUUUUCCUUC UAAAUGUGUA CAAUCUAGC 3'
                                10           20          30         40       49

Capture Probe 54

5' Biotin-GGCGAUGUCU GUUGCUAUUA UGUCUACUAU UCUUUCCCCU GCACUGUAC 3'

Binary Probe 58

```
       60                    67
  G—G
 G    CGTTATCTCG AC TAATAC 3'
 G    GCAATAGAGC TG ATTATGCT GAGTGATATC CCCTGGGGGG GCCTTCCCCC CCTGCTCCAC
  T—G
```

GCCCGTGGAG CATGCCCTCA AGCTGGCACT GAATTTTAAT CGTCCTTCTA CC 5'

Binary Probe 59

3' GGTCATTTTT GTCAAGTATG TCTCAGTGCC CGATCGCGAA AGCGCGAGAG GGTCCACTGC

GGAGCACTTC TCCGCGCTGG AAGCACGCAA AGCCACTGCG TGCTCTTGGC GGTGCGACGA

AGCGTCGCAC CGAGGAAGCG CGTCGGGCGA CGCGCTCCAC TGGGGGGCTT CCCCCCAAGG

SENSITIVE NUCLEIC ACID SANDWICH HYBRIDIZATION ASSAY

This is a continuation of application Ser. No. 08/157,367 filed on Nov. 23, 1993 now abandoned, which is a continuation of Ser. No. 08/006,073 filed on Jan. 15, 1993, now abandoned.

This invention was made with government support under grant number HL-43521 awarded by the National Institutes of Health. The United States government has certain rights in this invention.

This invention relates to nucleic acid hybridization assays, more particularly sandwich hybridization assays using oligonucleotide hybridization probes. Such assays have broad applicability, including assays for mutant genes, assays for pathogens in biological samples, and as says for an organism or virus in food, agricultural products or the environment.

BACKGROUND OF THE INVENTION

Oligonucleotide probes form extremely specific and stable complexes, known as "hybrids", with nucleic acid targets that contain target nucleic acid sequences complementary to the probes. Assays utilizing this principle generally have in common the steps of contacting nucleic acids in a sample with oligonucleotide probes under conditions that promote the formation of specific probe-target hybrids, washing away unhybridized probes, and measuring the number of probes that are hybridized (generally by measuring a signal generator associated with the probes) as an indication of the number of target nucleic acid sequences present (Gillespie & Spiegelman, 1965). For detection, a radioactive atom or a fluorescent moiety may be used. For detecting a small number of target molecules, the probes may contain an amplifiable group, such as an amplifiable reporter RNA (Chu et al., 1986), or alternatively an amplifiable recombinant RNA that contains an embedded probe sequence (Lizardi et al., 1988). If bacteriophage Qβ replicase is used for amplification, an RNA probe is amplified directly but a DNA probe may be amplified indirectly, that is, the probe is transcribed to prepare an RNA molecule that is then amplified directly (Martinelli et al., 1992). In this application we refer to probes as being "amplifiable" whether they are directly amplifiable or indirectly amplifiable.

Sandwich hybridization assays are known (Dunn & Hassell, 1977; Ranki et al., 1983; Syvanen et al., 1986). In nucleic acid sandwich assays, "capture probe" is used to bind the target, to which a "reporter probe" may or may not is also hybridized, to a solid surface. We sometimes refer to reporter probes as "signal probes." The capture probe hybridizes to the target at a site different from the "target sequence" where the reporter probes hybridizes. The resulting complexes include a target nucleic acid and a capture probe also hybridized to the target and, possibly, reporter probe(s) also hybridized to the target. The capture probe has one end, the "head," hybridizable to the target and a second end, the "tail," comprising a moiety that functions to bind the capture probe to a solid surface, such as the surface of a particle. Hybridization of the two probes is achieved by incubation with the target in solution, using an excess, generally a large excess, of both probes, followed by insolubilization, i.e., immobilization on a solid surface. Vigorous washing is used to remove excess reporter probes not hybridized to targets before detection of reporter probes.

Nucleic acid hybridization assays, including the sandwich assays described above, suffer from poor sensitivity caused by background or "noise" due to non-specific binding of reporter probes to the particles or other solid surfaces. Pretreatment of particles with albumin to block non-specific binding has been used to reduce this background or noise, as has covalent crosslinking of reporter probes to targets to permit more stringent washing (Yabusaki et al., 1986). Also, probe-target hybrids have been transferred from one solid surface to another by a procedure known as "reversible target capture"(Morrissey et al., 1989; Hunsaker et al., 1989). In reversible target capture, the capture probe-target-reporter probe complexes or hybrids are repeatedly released from particles, transferred to a new container containing new particles, recaptured (immobilized on the surfaces of the new particles via the tails of the capture probes) and vigorously washed. After a number of cycles of release, transfer, recapture and washing, the number of reporter probes bound nonspecifically to the final particles can be significantly reduced. The overall process is so effective at removing nonspecifically bound reporter probes that if a conventional reporter probe containing a radioactive atom or fluorescent moiety is utilized, no background can be detected (Thompson et al., 1989). Reversible target capture is, however, complex and time-consuming, machine-intensive and costly.

If amplifiable reporter probes (Lizardi et al., 1988) are used in conjunction with reversible target capture, target nucleic acids can be detected in samples at levels that are lower than the levels that can be detected with conventional reporter probes (Lomeli et al., 1989). The resulting assays have been reported to be the most sensitive hybridization assays known (Pritchard & Stefano, 1991).

None of the assays that include the background-reduction approaches described above completely eliminates background. Even the most sensitive of those assays utilizing reversible target capture are not sufficiently sensitive to take full advantage of the power offered by amplifiable reporter probes. It has been shown, for example, that approximately 10,000 nonspecifically bound reporter probes persist, even after three cycles of reversible target capture (Lomeli et al., 1989). This limits the sensitivity of the assay to samples that contain 100,000 target molecules or more. "Smart probes," that is, probes whose ability to generate a reporter signal depends upon hybridization properly to their targets (i.e., "target-dependent") have been proposed as a way to improve sensitivity. An example of a smart probe is one that contains a "molecular switch," wherein signal generation is dependent on a conformational change that takes place in the probe (Lizardi et al., 1992).

Another example of smart probes that have been disclosed is DNA "binary probes." A pair of DNA reporter probes hybridize adjacent to one another on the DNA target molecule, and one of the probes also functions to immobilize the hybrids on a solid surface, which permits washing. The probes can be ligated in a target-dependent fashion, namely ligation by a DNA-directed DNA ligase. The ligated product, a DNA "reporter molecule," may itself be detected, as when one reporter probe is used to immobilize the probe-target hybrids to a solid surface and the other reporter probe contains a radioactive atom or a fluorescent moiety (Landegren et al., 1988; Landegren and Hood, 1991). Alternatively, the DNA reporter molecule, immobilized on a surface as above by one of the binary probes, may be amplifiable, either directly or indirectly. Qβ replicase may be used to amplify the DNA reporter molecule directly, or the DNA reporter molecule may be transcribed, as by bacteriophage T7 RNA polymerase, to produce an RNA transcript that is a template for an RNA-directed RNA polymerase, such as Qβ replicase. In either case, exponential amplification produces a detectable product, whose detection is reported to indicate the presence of target nucleic acid (Martinelli et al., 1992). In known binary-probe assays, unhybridized immobilizing probes (i.e., one of the DNA binary probes) will be bound to the solid surface, just as unhybridized capture probes are in sandwich hybridization assays that utilize unary reporter probes.

Other assays use target-dependent, signal-generating reactions. Such reactions include the ligase chain reaction, LCR (Barany, 1991) the polymerase chain reaction, PCR (Erlich et al., 1991), the multienzyme amplification reaction, 3SR (Guatelli et al., 1990), the strand displacement amplification reaction, SDA (Walker et al., 1992), and the target-dependent replication reaction, TDR (Kramer & Lizardi, 1989).

It is an object of this invention to improve the sensitivity of nucleic acid hybridization assays, preferably to provide assays able to detect as few as 100 molecules of target nucleic acid and, preferably, without background, so that negative samples produce no signal.

It is another object of this invention to provide highly sensitive nucleic acid hybridization assays that do not suffer from the drawbacks of reversible target capture, that is, complexity and cost, along with being time-consuming and machine-intensive.

It is another object of this invention to provide highly sensitive assays compatible with exponential amplification to permit detection of rare target nucleic acids.

It is a particular object of this invention to provide highly sensitive nucleic acid hybridization assays that can be performed without a sophisticated laboratory, even under field conditions. Assays that do not require particles but include a simple-to-use solid, such as a dipstick, are especially desired in this regard.

It is another object of this invention to provide nucleic acid hybridization assays of improved sensitivity that are quantitative as well as qualitative.

These and other objects of this invention will be apparent from the description that follows.

SUMMARY OF THE INVENTION

In this description and in the appended claims, we sometimes refer to a molecule in the singular (e.g., "a capture probe"). The same applies to a complex (e.g., "a probe-target hybrid"). It will be understood that many copies are in fact used or made. We sometimes utilize the plural rather than stating "copies of," which is cumbersome. Persons skilled in the art will understand the meaning from the context.

The assays of this invention are sandwich nucleic acid hybridization assays, by which is meant nucleic acid hybridization assays that include immobilizing a target on the surface of a solid and washing the solid. The sandwich nucleic acid hybridization assays of this invention include at least one improvement, but preferably a combination of improvements to reduce background and improve sensitivity. One necessary feature of the assays is the use of a capture probe, by which we mean a probe that is not a reporter probe and that is used to immobilize either targets or reporter probe-target hybrids on the surface of a solid. More then one capture probe may be used (by which is meant at least two capture probes hybridizable to different sequences of the target), but at least one must be used. As applied to the instant invention, a "reporter probe" is limited to a probe that does not function to immobilize reporter-probe targets on a solid surface. Binary probe assays of the prior art do not include the use of a capture probe. Rather, they use one of the binary reporter probes as the means to immobilize reporter probe-target hybrids on a solid surface. Thus, the binary reporter probes used in the prior art binary probe assays are not "reporter probes" as that term applies to this invention, including the appended claims. We believe that this provides an unappreciated source of significant background, because many (typically $10^{10}$ to $10^{13}$) copies of the immobilizing reporter probe are not washed away, providing a high concentration favoring target-independent ligation. For that or some other reason, when a separate capture probe is used in a binary-probe assay, a significant improvement results.

A second feature of assays according to this invention, essential if targets alone or target-unary reporter probe hybrids are immobilized by capture probes and preferred if target-binary reporter probes hyrids are immobilized by capture probes, is the separation of targets or reporter probe(s)-target hybrids, as the case may be, from capture probes. Separation is accomplished by cleaving and then isolating the parts, that is, the target or reporter probe(s)-target hybrids, on the one hand. By "cleaving" is meant the breaking of on at least one phosphodiester bond at an appropriate site or sites in the target or in the capture probe.

We believe that retained capture probes are an unappreciated source of significant background, the many (typically $10^{13}$) copies of the capture probe provide sites for non-specific binding of reporter probes. The presence of capture probes also may cause significant background if present during detection of the reporter molecule, by fluorescence. If binary probes are used, capture-probe separation is preferred but is not essential for all embodiments of this invention. Use of binary probes, a separate capture probe, and stringent washing or reversible target capture will satisfy the sensitivity requirements in some cases.

The sensitivity-enhancing improvements of this invention are widely applicable to nucleic acid sandwich hybridization assays. The target may be DNA or RNA. The reporter probe or probes may be DNA or RNA. And the capture probe may be DNA or RNA. Additionally, the capture probe may contain chemically synthesized nucleotide analogues, such as 2'-O-methyl nucleotides.

In embodiments including separation of reporter probe(s)-target hybrids from capture probes, neither the nature of the reporter probe or probes nor the method of generating a detectable signal is critical. The probe may be unary or the probes may be binary. A unary smart probe may be used. The probe, or one of the binary probes, may contain a detectable moiety such as a radioactive atom or fluorescent moiety, or may include an enzyme that can be incubated with a colorless substrate to generate large numbers of colored products (Leary et al., 1983). Signal-generating techniques that utilize exponential amplication are preferred. The reporter probe or reporter molecule may be a template for an RNA-directed RNA polymerase (Lomeli et al., 1989). Other exponential amplication techniques that may be use are LCR, PCR, 3SR, SDA and TDR.

In embodiments that include the separation of targets from capture probes, which we refer to as "target purification," the assays must include a target-dependent signal-generating technique from the group of LCR, PCR, 3SR SDA and TDR.

The method of signal detection is not critical. Any appropriate method of signal detection may be used, such as radioactive counting or imaging, colorimetry, fluorescence or luminescence. Signal detection may be "on the fly" or over time for quantitative detection.

The type of solid surface on which the capture probe is immobilized is not critical. The solid may be a particle, a dipstick or the surface of a tube, for example. Any appropriate immobilization technique may be used, depending on whether or not immobilization is to be permanent or reversible, as in reversible target capture.

In embodiments employing binary probes, ligating in a target-directed manner is required but the method is not critical. A protein or ribozyme ligase may be used, as well as a non-enzymatic method such as chemical ligation, photo-induced ligation or self ligation.

In binary-probe embodiments employing separation of capture probes, ligation may precede or follow separation, although we prefer that ligation follow separation. Further, the manner in which capture probes are isolated is not critical. Procedures for isolating a solid phase from a liquid phase are well known, including typically aspiration and decanting. Separation from the capture probe (or capture probes) preferably is used without reversible target capture, but a combination of techniques may be employed. Without reversible target capture, the capture probe or probes may be permanently linked to a solid surface, such as when the tail of the capture probe has a biotin moiety and when the surface of the particle has covalently linked streptavidin molecules or avidin molecules to bind the biotin.

In embodiments including separation from capture probes, preferred embodiments utilize cleavage with ribonuclease H ("RNase H"), which cleaves RNA that is hybridized to DNA. A DNA capture probe is utilized for an RNA target, in which case the target is cleaved. An RNA capture probe is utilized for a DNA target, in which case the capture probe is cleaved.

Preferred embodiments of the invention are assays for RNA targets, because RNA targets suitable for detection are in most cases much more abundant in samples than corresponding DNA targets.

For highly sensitive assays, exponential amplification of reporter probes, either directly or indirectly (after transcription) is preferred. Assays that utilize amplifiable reporter probes can theoretically detect as little as one target molecule, since a single amplifiable reporter probe can serve as a template for the generation of billions of copies of itself (Levisohn and Spiegelman, 1968), leading to detection of the original reporter probe. The practical limit of detection is determined by the efficiency of the procedure that removes reporter probes that are not hybridized to target molecules. The sensitivity of assays that utilize reversible target capture is limited by the persistence of nonspecifically bound reporter probes, as indicated above. By the present invention, the level of persistence of nonhybridized reporter probes is markedly reduced, permitting assays of 1000-fold greater sensitivity and more.

Preferred embodiments of the invention utilize amplifiable binary probes; that is, probes that, when they are ligated to each other (and only when they are ligated to each other), form a reporter molecule that can be amplified exponentially, or that serves as a template for the generation of a molecule that can be amplified exponentially. In preferred embodiments of the invention, the set of reporter molecules that can be formed by the ligation of two binary probes includes: 1) recombinant RNAs that can be directly amplified exponentially by incubation with a compatible RNA-directed RNA polymerase (Miele et al., 1983); 2) DNA templates that comprise a promoter (or a sequence that can be extended by incubation with a DNA polymerase to form a promoter) and a sequence that encodes an RNA that can be transcribed by a DNA-directed RNA polymerase that is compatible with the promoter, so that the transcripts can then be amplified exponentially by incubation with a compatible RNA-directed RNA polymerase; and 3) DNAs or RNAs that can serve as templates for an exponential amplification reaction, such as LCR, PCR, 3SR, SDA and TDR.

Preferred embodiments of the invention utilize solid surfaces having streptavidin covalently linked to their surface and utilize capture probes that contain a biotin moiety so that the capture probes can be permanently bound to the surface of the particles. While preferred embodiments performed in our laboratory have utilized paramagnetic particles as the solid, an aspect of cleavage-separation according to this invention is that it permits assays that do not require a well-equipped laboratory. Dipsticks or reaction tubes (test tubes) may serve as the solid for an assay particularly adapted for performance under field conditions.

Preferred embodiments of the invention utilize binary probes, a separate capture probe, and separation of the binary probe-target hybrids from the capture probes (thus markedly reducing target-independent hybrids that form from binary probes that become nonspecifically bound to capture probes). In these preferred embodiments, a single wash cycle is sufficient to remove unhybridized binary probes, unhybridized cellular nucleic acids, and all other cellular material. Preferably, separation precedes ligation.

Preferred embodiments of the invention are assays for RNA targets using binary probes made of RNA, and a target-directed RNA ligase as disclosed in U.S. application Ser. No. 08/355,438 for Diagnostic Assays and Kits for RNA Using RNA-Directed RNA Ligase, naming S. Tyagi as inventor (hereinafter Tyagi Ser. No. 08/355,438) and U.S. application Ser. No. 08/315,191 for Diagnostic Assays and Kits for RNA Using RNA Binary Probes and a Ribozyme Ligase, naming P. Lizardi, S. Tyagi, U. Landegren, F. Kramer and J. Szostak as inventors (hereinafter Lizardi et al. Ser. No. 08/315,191), both of which are being filed on the same date as the instant application and both of which are incorporated herein by reference. Thus, one may use either a DNA-directed DNA ligase or a ribozyme ligase as the RNA-directed RNA ligase. Preferred as the DNA-directed DNA ligase is either bacteriophage T4 DNA ligase or E. coli DNA ligase. Preferred as the ribozyme ligase is Tetrahymena ribozyme ligase (Doudna & Szostak, 1989). Another embodiment of the invention utilizes RNA targets, binary probes made of DNA, and a suitable DNA ligase, such as T4 DNA ligase.

In preferred embodiments that utilize binary probes that, when they are ligated to each other (and only when they are ligated to each other), form a reporter molecule that can be amplified exponentially, either directly or indirectly, it is preferable that the molecule that can be exponentially amplified be a template for an RNA-directed RNA polymerase. In preferred embodiments, the RNA-directed RNA polymerase is a bacteriophage RNA-directed RNA polymerase, such as Qβ replicase, MS2 replicase, or SP replicase. In the most preferred embodiment, the RNA-directed RNA polymerase is Qβ replicase. In other preferred embodiments, the RNA-directed RNA polymerase is isolated from eucaryotic cells infected with a virus, such as cells infected with brome mosaic virus, cowpea mosaic virus, cucumber mosaic virus, or polio virus. In another preferred embodiment, the RNA-directed RNA polymerase is T7 RNA polymerase (Konarska and Sharp, 1989).

In embodiments in which the molecule that can be exponentially amplified is a recombinant RNA that serves as a template for Qβ replicase, it is preferred that the sequence of the recombinant template be derived from the sequence of an RNA in the following group: MDV-1 RNA, microvariant RNA, nanovariant RNA, CT RNA, RQ135 RNA, RQ120 RNA, and Qβ RNA. In the most preferred embodiment, the RNA is MDV-1 RNA.

In embodiments in which the molecule that can be exponentially amplified is a recombinant RNA that comprises an MDV-1 RNA sequence into which a probe sequence has been embedded (Lizardi et al., 1988; and Lomeli et al., 1989), the probe sequence can be inserted at any location within the sequence of MDV-1 RNA. Although preferred locations for insertion of a sequence into MDV-1 RNA (and indeed for insertion of a probe sequence into any other RNA template for an RNA-directed RNA polymerase) are those that occur in hairpin loops located on the exterior of the molecule in regions located away from regions that are required for replication (Miele et al., 1983), the probe sequence can be inserted into any location and the resulting recombinant can be tested to see if it is exponentially replicatable. Methods for identifying potential hairpin loops that can serve as suitable insertion sites, methods for constructing the desired recombinant RNAs, and methods for testing the resulting recombinants to see whether they can be replicated exponentially by incubation with a compatible RNA-directed RNA polymerase, are known to those of ordinary skill in the art.

In preferred embodiments, the exponentially amplifiable recombinant RNAs contain an inserted probe sequence that is between 30 and 80 nucleotides long. In a most preferred embodiment, the exponentially amplifiable recombinant RNAs contain an inserted probe sequence that is about 40 nucleotides long. In preferred embodiments, the way in which the sequence of the exponentially amplifiable recombinant RNA is divided into "halves" for inclusion into the sequence of each binary probe, is that the sequence of the exponentially amplifiable recombinant RNA is divided about in the middle of the probe sequence. To illustrate this concept, imagine that the exponentially amplifiable recombinant RNA is based on a sequence that is 220 nucleotides long and the recombinant contains an embedded probe sequence that is 40 nucleotides long and that probe sequence is inserted between nucleotides 60 and 61 of the 220-nucleotide-long sequence (resulting in a sequence that is 260 nucleotides long). Then, in a preferred embodiment, the left probe would comprise a sequence that consists of the first 60 nucleotides of the 220-nucleotide-long sequence and immediately adjacent to it (at one end of the binary probe, for instance, the 3' end) would be the first 20 nucleotides of the 40-nucleotide-long embedded probe sequence; the right binary probe would comprise the second 20 nucleotides of the 40-nucleotide-long embedded probe sequence (at the 5' end of the binary probe) and immediately adjacent to it would be the remaining 160 nucleotides of the 220-nucleotide sequence.

When the binary probes are made of RNA, and they are to be synthesized by transcription from DNA templates, it is preferable that the binary probe that has a probe sequence at its 5' end begin with a guanosine, because guanosine is preferred as the 5' nucleotide in syntheses that utilize known DNA-directed RNA polymerases.

When the binary probes are made of RNA, and a ribozyme ligase is utilized to link the binary probes, it is necessary that the binary probe that has a probe sequence at its 5' end contain an additional guanosine at its 5' end. This guanosine is removed by the ribozyme when the binary probes are ligated to each other.

When the binary probes are made of DNA and one of them possesses a promoter (or a sequence that can be extended by incubation with a DNA polymerase to form a promoter), and when they are ligated together, the resulting DNA possesses a sequence that encodes an RNA that can be transcribed by an RNA polymerase compatible with the promoter, then there are a number of preferred embodiments of how the binary probes should be designed. These preferred embodiments include: 1) a binary probe that encodes a promoter sequence should have a hairpin structure at its 3' end, the stem of which either comprises a (double-stranded) promoter or can be extended by incubation with a DNA polymerase to form a (double-stranded) promoter, thus eliminating the requirement that a separate complementary DNA strand be present to hybridize to the sequence encoding the promoter to form a functional promoter; 2) it is preferable that when a binary probe contains a hairpin structure at its 3' end that comprises a (double-stranded) promoter, that the 3' end be used as a primer for its own extension by incubation with a DNA polymerase, resulting in the generation of a double-stranded template for transcription by a compatible DNA-directed RNA polymerase, thus eliminating the inhibitory effects of the presence of hairpin structures on transcription (had the template remained single-stranded); and 3) it is preferred that a binary probe that encodes a promoter sequence should not encode the region of the amplifiable recombinant RNA that comprises the binding site of the compatible RNA-directed RNA polymerase, resulting in a design that ensures that the short transcripts that can be synthesized from this binary probe (if it is not ligated) will not be able to be replicated.

And finally, in preferred embodiments of the invention, preferred methods of detecting include: 1) the incorporation of a radioactive nucleotide into RNA during amplification; and 2) the binding of a molecule, such as ethidium bromide or propidium iodide, that becomes fluorescent when it binds to amplified RNA.

Using amplifiable RNA binary probes, separate DNA capture probes, cleavage of the reporter probes-target hybrids from the capture probes by incubation with RNase H and isolation of the reporter probes-target hybrids from particles containing the capture probes, an assay according to this invention has been demonstrated to detect, qualitatively and quantitatively, RNA target molecules in amounts ranging from 100 to 10,000,000 molecules per sample, and as few as one HIV-1-infected human lymphocyte cell in a sample containing 100,000 uninfected human lymphocyte cells with no background signal for samples containing no target molecules and for samples containing no infected cells. This level of sensitivity is achieved without resort to reversible target capture.

This invention also includes diagnostic kits for preselected targets. Kits according to this invention may contain a unary reporter probe, at least one capture probe, a cleaving agent, and instructions for carrying out a diagnostic assay. Kits may include a pair of binary probes, at least one capture probe and instructions. Preferred kits include a pair of binary probes, at least one capture probe, a cleaving agent and instructions. Preferred kits may also include enzymes (e.g., RNase H, T4 DNA ligase and Qβ replicase) and, optionally, other reagents.

A detailed description of numerous embodiments of this invention, including particularly preferred embodiments, follows in the Detailed Description. Neither the Detailed Description nor the examples are intended to limit the scope of the invention or the claims to the preferred embodiments.

BRIEF DESCRIPTION OF THE DRAWINGS

FIG. 2 shows the sequences of the probes of Example 1.

FIG. 8 shows the sequences of the probes of Example 2 SEQ ID Nos. 5–8.

DETAILED DESCRIPTION

Figure 1:
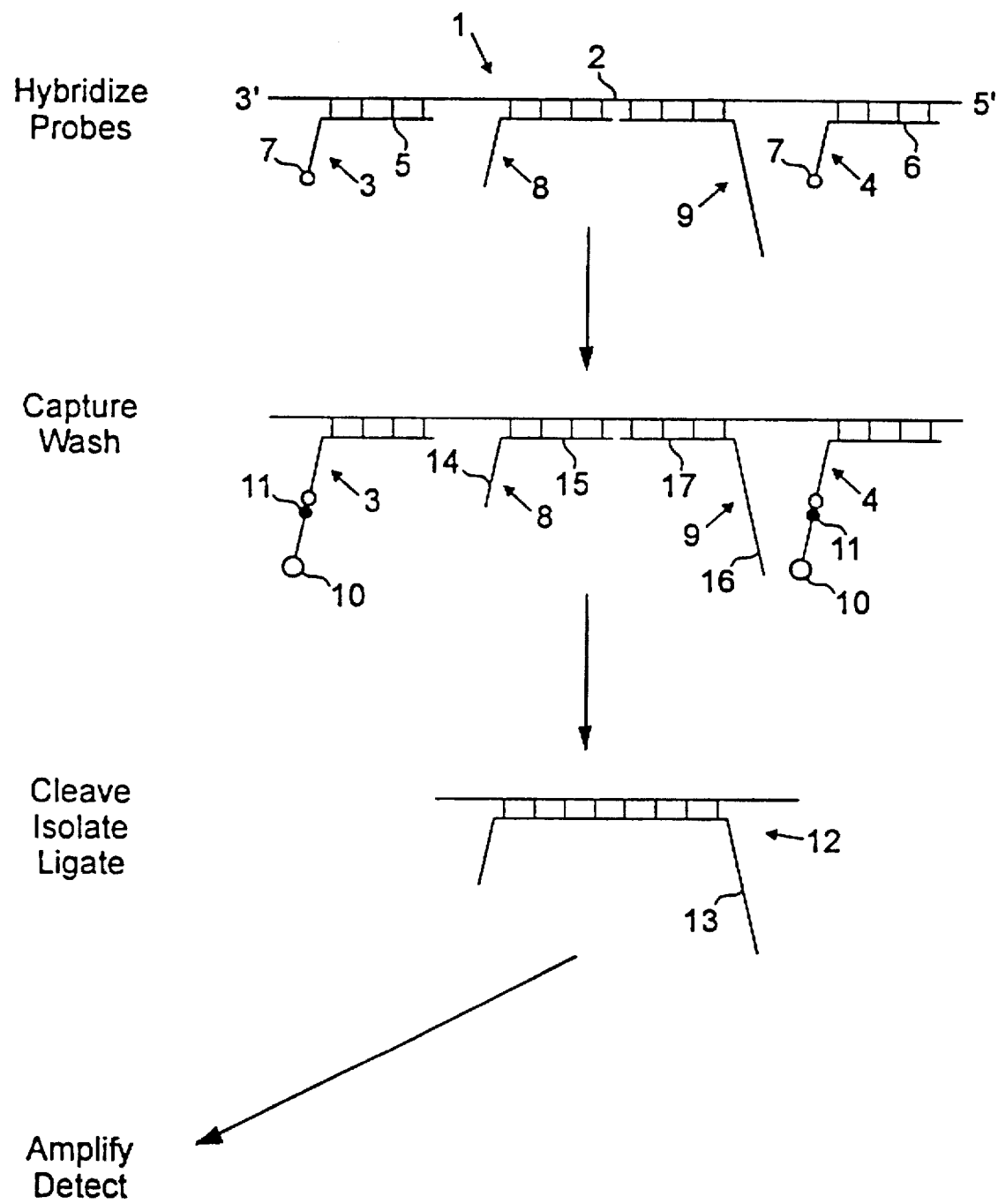
FIG. 1 depicts the assay of Example 1.

As stated, this invention is broadly applicable to nucleic acid sandwich hybridization assays utilizing reporter probes and separate capture probes, that is, capture probes that are not reporter probes.

At least one capture probe is used, optionally more than one, as in our most preferred, highly sensitive assay described below in Example 1. The use of two capture probes rather than one increases the chance that a given target molecule will be captured, because the act of capturing is not 100% efficient.

It is desirable that the capture probe-target hybrids be stable, so that hybrids are not lost during the assay. Persons skilled in the art are able to select a hybrid length sufficiently long to withstand the processing conditions of a particular assay. Generally, we prefer capture probe-target hybrid lengths of 30–50 basepairs, which defines the length of the head (in nucleotides) of the capture probe. The tail of the capture probe or probes is used to immobilize the capture probe and its hybrids to a solid surface, either permanently or reversibly. If separation of the capture probe or probes according to this invention is used, we prefer that the tail of the capture probe be a biotin group that will react with a streptavidin-coated solid surface. Between the head of a capture probe and its tail is a spacer, generally an oligonucleotide sequence. We prefer assays in which hybridizations and ligations are performed in solution, that is, when targets are not immobilized on a solid surface. Particularly for such preferred assays, the spacer may be quite short. Preferred spacers are 3–8 nucleotides in length.

The cleavage step and the cleaving agent or agents that are appropriate depend on the nature of the target nucleic acid, the nature of the capture probe, and the nature of the reporter probes, if present. In general, there are eight different situations that can occur. Table 1 below identifies each situation by a Roman numeral:

TABLE 1

| Situation | Target | Capture Probe | Reporter Probe |
|-----------|--------|---------------|----------------|
| I    | RNA | RNA | RNA |
| II   | RNA | RNA | DNA |
| III  | RNA | DNA | RNA |
| IV   | RNA | DNA | DNA |
| V    | DNA | RNA | RNA |
| VI   | DNA | RNA | DNA |
| VII  | DNA | DNA | RNA |
| VIII | DNA | DNA | DNA |

The following nine cleavage techniques illustrate the variety of ways that reporter probe-target hybrids can be released from capture probes by cleaving agents, with reference to the situations in Table 1.

1. Cleavage of an RNA target with a single-strand-specific ribonuclease (such as ribonuclease A or ribonuclease T1) (situation IV). Because these ribonucleases do not cleave DNA, nonspecifically bound reporter probes are not released from the capture probes. An embodiment of this technique is described in Example 6. This cleavage technique is not applicable to target purification.

2. Site-specific cleavage of an RNA target with a ribozyme (situations I, II, III and IV). Because the ribozyme can be designed to cleave a particular site in the target RNA (Haseloff & Gerlach, 1988), a third element of specificity is added to the assay. Cleavage of the target RNA is designed to occur in the region between the sites in the target where the capture probe and the reporter probe bind, thus releasing the reporter probe-target hybrid from the solid surface. Two embodiments of this technique are described in Example 3.

3. Site-specific cleavage of an RNA target with ribonuclease III ("RNase III"), utilizing a site-identifying probe made of RNA (situation IV). The site-identifying probe is designed to be complementary to a pre-selected site in the target that occurs in the region between the sites where the capture probe and the reporter probe bind. The site-identifying probe is included in the original hybridization mixture. Because ribonuclease III only cleaves double-stranded RNA at particular sequences (Krinke & Wulff, 1990), a third element of specificity is added to the assay. Cleavage of the target RNA occurs in the region between the sites where the capture probe and the reporter probe bind, thus releasing the reporter probe-target hybrid from the solid surface. We found experimentally that ribonuclease III will cleave almost all double-stranded RNAs if they are sufficiently long. For this reason, the use of ribonuclease III in situations I, II, III is not preferred. An embodiment of this technique is described in Example 4.

4. Site-specific cleavage of an RNA target with ribonuclease H, utilizing a site-identifying probe made of DNA (situation I). The site-identifying probe is designed to be complementary to a pre-selected site in the target that occurs in the region between the sites where the capture probe and the reporter probe bind. The site-identifying probe is included in the original hybridization mixture. Because ribonuclease H only cleaves RNA that is hybridized to DNA, cleavage is limited to the site where the site-identifying probe binds. The use of a site-identifying probe introduces a third element of specificity into the assay. Cleavage of the target RNA occurs in the region between the sites where the capture probe and the reporter probe bind, thus releasing the reporter probe-target hybrid from the solid surface.

5. Site-specific cleavage of a DNA target with a restriction endonuclease, utilizing a site-identifying probe made of DNA (situations V, VI, VII and VIII). The site-identifying probe is designed to be complementary to a pre-selected site in the target that occurs in the region between the sites where the capture probe and the reporter probe bind. The site-identifying probe is included in the original hybridization mixture. Because restriction endonucleases only cleave double-stranded DNA at particular sequences, a third element of specificity is added to the assay. Cleavage of the target DNA occurs in the region between the sites where the capture probe and the reporter probe bind, thus releasing the reporter probe-target hybrid from the solid surface.

6. Cleavage of an RNA target with ribonuclease H at the site where the head of a DNA capture probe is bound (situation III). Because ribonuclease H only cleaves RNA that is hybridized to DNA, cleavage is limited to this specific site. By appropriate design of the capture probe, as persons skilled in the art will readily appreciate, cleavage of the target RNA destroys the capture probe-target hybrid, releasing the reporter probe-target hybrid from the solid surface. An embodiment of this preferred technique is described in Example 1.

7. Cleavage of an RNA capture probe with ribonuclease H at the site where a DNA target is bound (situation VI). Because ribonuclease H only cleaves RNA that is hybridized to DNA, cleavage is limited to this specific site. By appropriate design of the capture probe, as persons skilled in the art will readily appreciate, cleavage of the head of the capture probe destroys the capture probe-target hybrid, releasing the reporter probe-target hybrid from the solid surface. An embodiment of this technique is described in Example 8.

8. Cleavage of an RNA target with ribonuclease III at the site where the head of an RNA capture probe is bound (situation II). Because ribonuclease III only cleaves double-stranded RNA, cleavage is limited to this specific site. Cleavage of both strands of RNA in the capture probe-target hybrid releases the reporter probe-target hybrid from the solid surface. An embodiment of this technique is described in Example 5.

9. Cleavage of a DNA target with a restriction endonuclease at the site where the head of a DNA capture probe is bound (situations VII and VIII). Cleavage of both strands of DNA in the capture probe-target hybrid releases the reporter probe-target hybrid from the solid surface. An embodiment of this technique is described in Example 7.

The assays of this invention utilize certain assay techniques that will be readily understood by persons skilled in nucleic acid sandwich hybridization assays.

The techniques will be described for embodiments in which reporter probe(s)-target hybrids are separated from capture probes. A large excess of reporter probes and capture probes is added to a sample under conditions promoting hybridization. Hybridization preferably occurs in solution. Pre-immobilization of capture probes on a solid surface is not preferred but is not excluded. Immobilization via the tails of the capture probes follows, after which the supernatant is removed and the solid washed, preferably vigorously, and a clean supernatant is added. When used, cleavage releases reporter probe-target hybrids into the supernatant, which is then isolated from the solid containing the capture probes, as by decanting or aspiration. When binary probes are used, they are ligated, preferably at this point in the assay. Amplification, if desired, and detection follow. Several detection methods are well known, including radiation (use of a radioactive nucleotide triphosphate), colorimetry (e.g., use of an enzyme that can cause a color change in a substrate) fluorescence (e.g., use of a dye such as propidium iodide), and luminescence (e.g., use of an alkaline phosphatase substrate that releases photons upon cleavage). Detection can be qualitative or quantitative, as will be discussed below.

Preferred embodiments utilize isolation procedures in which the capture probes that are bound to the particles can be physically removed from the solution containing the released reporter probe-target hybrids. If non-paramagnetic particles are used, a centrifuge can be used to force the particles to the bottom of the test tube and the supernatant containing the reporter probe-target hybrids can be removed by aspiration; or if the particles are paramagnetic (which is preferred because a centrifuge is not needed), a magnet can be used to draw the particles to the walls of the test tube and the supernatant containing the reporter probe-target hybrids can be removed.

Preferred embodiments of the invention utilize paramagnetic particles containing streptavidin covalently linked to their surfaces and capture probes that contain a biotin moiety at their tails (so that the capture probes can be permanently linked to the surface of the particles or beads).

Preferred embodiments of assays according to this invention, particularly for highly sensitive assays, are assays for RNA targets and utilize RNA reporter probes, which have the potential of generating an easily detectable amplified signal from even a single reporter molecule, at least one DNA capture probe and ribonuclease H.

Particularly preferred embodiments of the invention use reporter probes that are binary hybridization probes, neither of which functions to immobilize the target on a solid surface, which can only be ligated to each other in a target-dependent reaction if they are correctly hybridized adjacent to one another, and which, when they are ligated, form a recombinant reporter molecule that is exponentially amplifiable by Qβ replicase, either directly (serving as a template for the replicase) or indirectly (serving as a transcription template, the transcripts then serving as templates for the replicase). Most preferred are assays for RNA targets utilizing DNA capture probes and RNA binary probes. The methods of this invention are particularly attractive when using binary hybridization probes, wherein the ligation and amplification reactions are carried out without interference from the presence of solid surfaces. In contradistinction, previous methods that utilize binary hybridization probes utilized one of the binary probes to immobilize probe-target hybrids (Landegren et al., 1988; and Martinelli et al., 1992); and these methods suffer from the presence of solid surfaces during ligation.

One important objective of this invention is an assay that will detect very few target molecules, as few as 100 in a sample, without a background signal from negative samples. Example 1 illustrates a preferred embodiment of such an assay. The assay of Example 1 is an assay for an RNA target utilizing RNA binary reporter probes whose ligation produces an RNA reporter molecule that is directly amplifiable by an RNA-directed RNA polymerase, in this case Qβ replicase. Use of a separate capture probe permits washing away unused copies of both binary reporter probes before ligation of the binary reporter probes. Ligation is target-dependent. Target-independent ligation, which we believe to be a source of background, is greatly reduced by washing away both binary reporter probes rather than having one binary reporter probe immobilized on a solid surface in high concentration.

Even so, nonspecifically bound reporter probes remain as a source of background. Reversible target capture is one technique that may be used to reduce this source of background to a low level that will be acceptable for many assays. However, reversible target capture has significant drawbacks. First, it is costly, time-consuming, complex and machine intensive. Second, there is the possibility of losing some reporter probe-target hybrids in every round of reversible target capture. Third, we believe that capture probes themselves provide sites for non-specific binding of reporter probes. In reversible target capture all capture probes, the few bound to targets and the great excess not bound to targets, are retained.

The assay of Example 1 addresses all of those drawbacks. Reporter probe-target hybrids are separated from both capture probes by cleaving the reporter probe-target-capture probe hybrids with ribonuclease H. This cleavage releases the reporter probe-target hybrids and leaves the capture probes, and reporter probes nonspecifically bound thereto, behind on the surface of the solid (in Example 1 the solid is paramagnetic particles), permitting an easy physical separation. Ligation is performed after this separation. Amplification directly with Qβ replicase and detection follow.

By this combination of steps, the background due to nonspecific hybridization was reduced to zero. The resulting assay was sufficiently sensitive to detect as little as 100 target nucleic acid molecules. And finally, and most significantly, by combining the use of a smart probe, e.g., binary reporter probes, and a separate capture probe with a step that separates reporter probe-target hybrids from capture probes, it was possible to carry out these extremely sensitive assays without resort to the costly, time-consuming, complex, and machine-intensive reversible target capture procedure. Consequently, sensitive hybridization assays can be carried out on dipsticks, utilizing simple washing techniques that are commonly used in clinical immunoassays.

As stated earlier, this invention also includes kits for performing assays according to this invention. A preferred kit may contain some or all of the following items:

1. 5M guanidine thiocyanate (GuSCN) buffer for the lysis of cells in clinical samples;
2. A mixture containing capture probes and reporter probes, preferably binary probes, for a preselected nucleic acid target;
3. A solid, such as a dipstick, reaction tube or paramagnetic particles, with streptavidin covalently bound thereto;
4. A magnetic separation device;
5. Nucleotides;
6. Ribonuclease H, T4 DNA ligase and Qβ replicase;
7. Buffers for ligation and amplification;
8. Reagents for detecting the amplified reporters, such as radioactive alpha-$P^{22}$-cytidine triphosphate or propidium iodide;
9. If the binary probes are made of DNA, the Klenow fragment of E. coli DNA polymerase and T7 RNA polymerase; and
10. Instructions for performing an assay according to this invention.

A bare kit may contain only binary reporter probes, at least one capture probe and instructions, items 2 and 10. Another kit may contain a unary reporter probe, at least one capture probe and a cleaving agent, preferably ribonuclease H, as well as instructions, items 2, 6 and 10. A more complete kit for preferred assays will contain binary reporter probes, at least one capture probe, plus at least items 1, 3, 6 and 10, as well as item 9 when appropriate. A kit containing at least items 1-3 and 5-10 (item 9 only where appropriate), where the solid is a dipstick or reaction tube, is particularly useful for assays to be performed outside a well-equipped laboratory.

As stated earlier, certain embodiments of this invention are types of nucleic acid sandwich hybridization assays that include target purification.

The description in the preceding paragraphs regarding capture probes, cleavage steps and isolation steps in equally applicable to target purification with the exception that reporter probes need not be taken into account, because they are not present during target purification. Preferred targets for assays including target purification according to this invention are RNA targets, because RNA targets suitable for detection are in most cases much more abundant in samples than corresponding DNA targets.

When LCR follows target purification, we especially prefer the use of RNA probes and an RNA-directed ligase, such as T4 DNA ligase, (a protein molecule,) or Tetrahymena ribozyme ligase (an RNA molecule.) If the latter is used, the LCR probes have hybridization lengths no longer than aout nine nucleotides.

A preferred kit for an assay according to this invention that includes target purification may contain some or all of the following items:

1. 5M GuSCN;
2. DNA capture probe(s) for a preselected RNA target;
3. A solid, such as paramagnetic particles, coated with streptavidin;
4. A magnetic separation device;
5. Ribonuclease H;
6. RNA LCR primers;
7. T4 DNA ligase;
8. LCR buffer; and
9. Instructions.

A complete kit will include all of items 1-9. A bare kit will include at least items 2, 6 and 9. A universal kit for target purification in embodiments of assays according to this invention will include at least items 2 and 9, preferably also items 3 and 5.

EXAMPLES

Example 1
RNA Target, RNA Binary Probes, DNA Capture Probes and Ribonuclease H Cleavage The present invention reduces the background in sandwich hybridization assays, while simultaneously simplifying the format of the assays. This embodiment, which employs RNA binary probes, has led to extremely sensitive assay depicted generally in FIG. 1 for the detection of an RNA target, illustrated here by human immunodeficiency virus ("HIV") RNA. The target sequence 2 of target 1 is located in the integrase region of HIV RNA. The assay begins by dissolving the sample in 5M guanidine thiocyanate (GuSCN). A mixture of four different nucleic acid probes is then added to the sample. These probes hybridize to the HIV RNA, as shown in FIG. 1. Two of the probes are capture probes SEQ ID Nos: 1,2 3, 4 made of DNA. Each capture probe has a hybridization sequence 5 or 6 at its 3' end that is complementary to the target 1. Capture probes SEQ. ID Nos: 1,2 3, 4 also have a biotin moiety 7 at their 5' ends. The other two probes SEQ ID Nos: 4,3 8, 9 are binary reporter probes made of RNA. After hybridization, the hybrids are captured on the surface of paramagnetic particles 10 coated with streptavidin 11, which binds tightly to the biotin moiety 7 of the capture probes. The paramagnetic particles 10 are then washed extensively to remove unhybridized binary probes. RNase H is then added to cleave the target RNA in the region where it is hybridized to the capture probes. Cleavage of the target RNA frees the binary probes-target hybrids 12 (shown in FIG. 1 after ligation) from the capture probes.

The cleavage release step is quantitative and specific. The binary probes that nonspecifically adhere to the DNA capture probes or to the surface of the paramagnetic particles (i.e., sources of the background signal) are not released by this cleavage. The paramagnetic particles 10 are discarded. Assays utilizing this target-dependent release achieve, in a single step, a signal-to-noise ratio that is similar or superior to the signal-to-noise ratio achieved in the multi-step reversible target capture method.

In the supernatant, pairs of binary probes that are correctly hybridized adjacent to one another on their targets are ligated to each other in a target-dependent manner. The ligated probes 13 are then amplified by incubation with Qβ replicase. The amplified signal is strictly dependent on the presence of the target, and the level of the signal as a function of time can be used to determine quantitatively the number of molecules of HIV RNA in the initial sample. By combining a target-dependent RNase H-mediated release step with a target-dependent ligation step, background signal is completely eliminated.

A. Synthesis of the Probes

The capture probes used in this example (FIG. 2 SEQ ID Nos: 1–4) have three functional parts. A head of 40–50 nucleotides which hybridize to the preselected target, a spacer of about 4 nucleotides, and a tail that binds tightly to the solid surface. We chose the tail to be a biotin moiety and covalently linked it to the 5' end of each capture probe. The biotin moiety can be attached anywhere in the capture probe, including at the 3' end and internally. The tail can be made up of some other affinity reagent, such as a homopolynucleotide.

FIG. 1 shows the manner in which capture probes 3, 4 SEQ ID Nos: 1,2 bind to target 1. Two different capture probes were used, rather than one, in order to increase the efficiency of capture and increase the stringency of release of the binary probe-target complexes. The two capture probes 3, 4 SEQ ID Nos: 1,2 bind to target 1 on either side of the target sequence 2 to which the binary probes bind. Hybridization sequence 5 of capture probe 3 SEQ ID Nos: 1 is complementary to region 4415–4458 of HIV genomic RNA, and hybridization sequence 6 of capture probe 4 SEQ ID Nos: 2 is complementary to region 4808–4852 of HIV genomic RNA. FIG. 2 SEQ ID Nos: 1,2 shows the sequences of the two capture probes 3, 4 SEQ ID Nos: 1,2 used in this example. Underlines indicate hybridization sequences 5, 6 that are complementary to the target RNA. Both of the capture probes were prepared on a DNA synthesizer.

The desired reporter molecule of this particular embodiment requires the ligation of two binary probes, as shown in FIG. 1. The use of binary probes is a preferred embodiment. FIG. 1 illustrates the design of binary reporter probes 8, 9 SEQ ID Nos: 4,3. The 5' end 14 of probe 8 SEQ ID Nos: 4 consists of the first sixty-nine nucleotides of the replicatable probe for HIV used in our previous studies (Lomeli et al., 1989). The next twenty-three nucleotides are probe sequence 15, which is complementary to region 4596–4618 of HIV genomic RNA. The 5' end of probe 9 SEQ ID Nos. 3 consists of 19-nucleotide probe sequence 17, which is complementary to region 4577–4595 of HIV genomic RNA. The remainder 16 of probe 9 corresponds to nucleotides 95–280 of the replicatable probe for HIV used in our previous studies (Lomeli et al., 1989). FIG. 2 shows the sequences of binary probes 8, 9. Underlines indicate hybridization sequences 15, 17 that are complementary to the target sequence. Neither of these molecules is a good replicator when incubated with Qβ replicase, but if they are ligated to each other, they form an exponentially replicatable reporter molecule.

Figure 3:
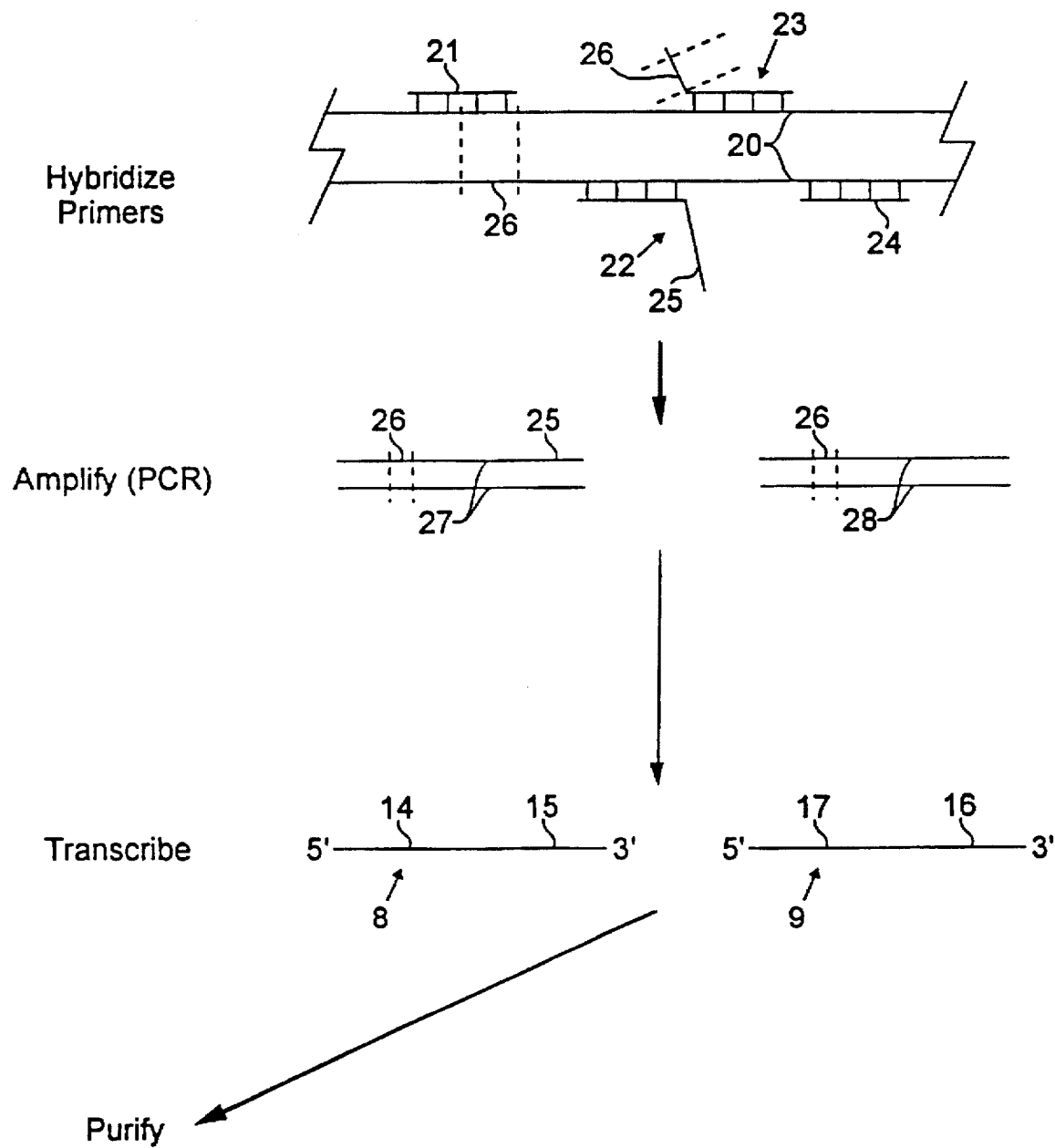
FIG. 3 depicts the preparation of binary probes of Example 1 SEQ ID Nos. 1–4.

Binary probes 8, 9 were prepared by transcription from DNA templates generated in a polymerase chain reaction (PCR) shown in FIG. 3. The plasmid 20 described in Lomeli et al., 1989 at page 1827, which we call plasmid pT7MDVHIV20, was used as the source of MDV sequences in the PCR reactions. The relevant section of the plasmid is shown in FIG. 3. It is, of course, double-stranded. Four PCR primers 21, 22, 23 and 24 were designed in such a way that they contributed additional sequences to the PCR products 27, 28 that were not present in plasmid 20, but which were required. PCR product 27 is generated from primers 21, 22. PCR product 28 is generated from primers 23, 24. Primer 22 provided the terminal twenty-three nucleotides 25 in the template for probe 8. Primer 23 provided T7 promoter 26 at the 5' end of the template for probe 9. (Plasmid 20 provided a T7 promoter in the region of primer 21.) Probe 8 was transcribed in the usual manner from its PCR template, but the synthesis of probe 9 required a modification in the conditions of transcription by T7 RNA polymerase. The donor of the phosphate group in a ligation reaction, in this case probe 9, must contain a single phosphate at its 5' end. RNA molecules prepared by transcription usually have a triphosphate at their 5' ends. In order to synthesize probe 9 with a single phosphate group at its 5' end, a ten-fold excess of guanosine 5'-monophosphate over the nucleoside 5'-triphosphates was included in the transcription reaction. This lead to the incorporation of guanosine 5'-monophosphate at the first position of the probe 9. As a result, the copies of probe 9 possessed the required monophosphate at their 5' ends. After transcription, each of the binary probe RNAs 8, 9 was purified by preparative polyacrylamide gel electrophoresis. The RNA was eluted directly from the gel slice into a 2M guanidine thiocyanate (GuSCN) solution.

We have discovered since this example was performed that probe 9 can be improved by using a twenty-fold excess of guanosine 5'-monophosphate rather than the ten-fold excess reported above. Efficiency of ligation triples, from 10% to 30%, when the greater excess is used.

B. Hybridization, Capture, Washing, and Release

The assay of this example has been performed on samples containing known amounts of HIV RNA molecules. An RNA corresponding to the mRNA of the integrase gene of HIV was used as a model target. This RNA was prepared by transcription from linearized plasmid pGEM-integrase, that was prepared in our laboratory. Eight tubes containing differing amounts, for example, 10000000, 1000000, 100000, 10000, 1000, 100, 10, and 0 molecules, of integrase RNA in 50 microliters of 2M GuSCN were prepared by serial dilution. A 2M GuSCN solution (50 microliters) containing $10^{13}$ molecules of each of the capture probes and $2\times10^{10}$ molecules of each of the binary probes was added to each tube. Hybridization was carried out by incubation at 37 degrees centigrade for one hour. A 30-microliter suspension of paramagnetic particles coated with streptavidin (Promega) was then added to this hybridization mixture. The probes-target hybrids were captured on the surface of the paramagnetic particles by a 10-minute incubation at 37 degrees centigrade. The particles were washed with 2M GuSCN four times, with 300 mM KCl three times, and finally with 1× ligase buffer (66 mM Tris-HCl, pH 7.5, 5 mM MgCl$_2$, 1 mM DTT, 1 mM ATP) two times. After washing, one unit of E. coli RNase H (Pharmacia) dissolved in 50 microliters of 1× ligase buffer was added. The binary probes-target hybrids were released from the surface of the paramagnetic particles by a 10-minute incubation at 37 degrees centigrade. The tubes containing the mixture were placed in the magnetic field provided by a magnetic separation device to draw the paramagnetic particles to the walls of the test tubes. The supernatant was then separated from the paramagnetic particles by aspiration and placed into a fresh tube. The probe-target hybrids were then incubated with T4 DNA ligase in order to ligate the binary probes that were correctly hybridized to targets. Ligation was carried out in 40 microliters of the supernatant by the addition of 40 units of T4 DNA ligase and incubation at 37 degrees centigrade for one hour.

The assay of this example has also been performed on samples containing known amounts of HIV-infected cells. In order to demonstrate the specificity and sensitivity of this assay with clinical samples, human peripheral lymphocytes were infected with HIV. These infected cells were serially diluted with uninfected human peripheral lymhocytes. Eight tubes were prepared, containing differing amounts, for example, 600000, 60000, 6000, 600, 60, 6, 0, and 0 infected cells. Each of these tubes had the same total number of cells, for example, 600000. The tubes were centrifuged and the supernatant was removed. 240 microliters of 5M GuSCN was added to each tube. The tubes were then incubated for 2 hours at 37° C. in order to lyse the cells. After lysis, 40 microliters from each tube were assayed. A 60 microliter solution containing all four probes was added to the lysate. The addition of this solution reduced the GuSCN concentration in the lysate to 2M. Hybridization and all subsequent reactions were carried out the same as described in the previous paragraph.

C. Amplification The reporter molecules, comprising ligated binary probes, were then amplified by incubation with Qβ replicase. It is not necessary to melt apart the reporter molecule-target hybrids prior to amplification. A mixture containing all of the components of the replication reaction was added to each of the eight tubes. The final reaction mixture (120 microliters) was 45 mM Tris-HCl (pH 8), 10 mM $MgCl_2$, 400 micromolar ATP, 400 micromolar GTP, 400 micromolar UTP, 400 micromolar alpha-$P^{32}$-CTP, and contained 50 micrograms per milliliter Qβ replicase. Each reaction was incubated at 37 degrees centigrade, and 4-microliter samples were withdrawn from each reaction every minute in the interval between 10 to 31 minutes of incubation. Each sample was mixed with a 45-microliter stop solution (120 mM NaCl, 20 mM EDTA, and 3 microgram per ml proteinase K). This solution stops replication by sequestering the required magnesium ions. The stop solutions were arranged in titerplates before addition of the samples. The RNA in each stopped reaction was separated from the unincorporated nucleoside triphosphates by precipitating the RNA in an acidic solution (360 mM phosphoric acid, 20 mM sodium pyrophosphate, and 2 mM EDTA), trapping the precipitate on a blotting membrane (Zeta Probe, Biorad), and then washing the membrane with the acidic solution. The RNA on the blots was visualized by autoradiography.

Figure 4:
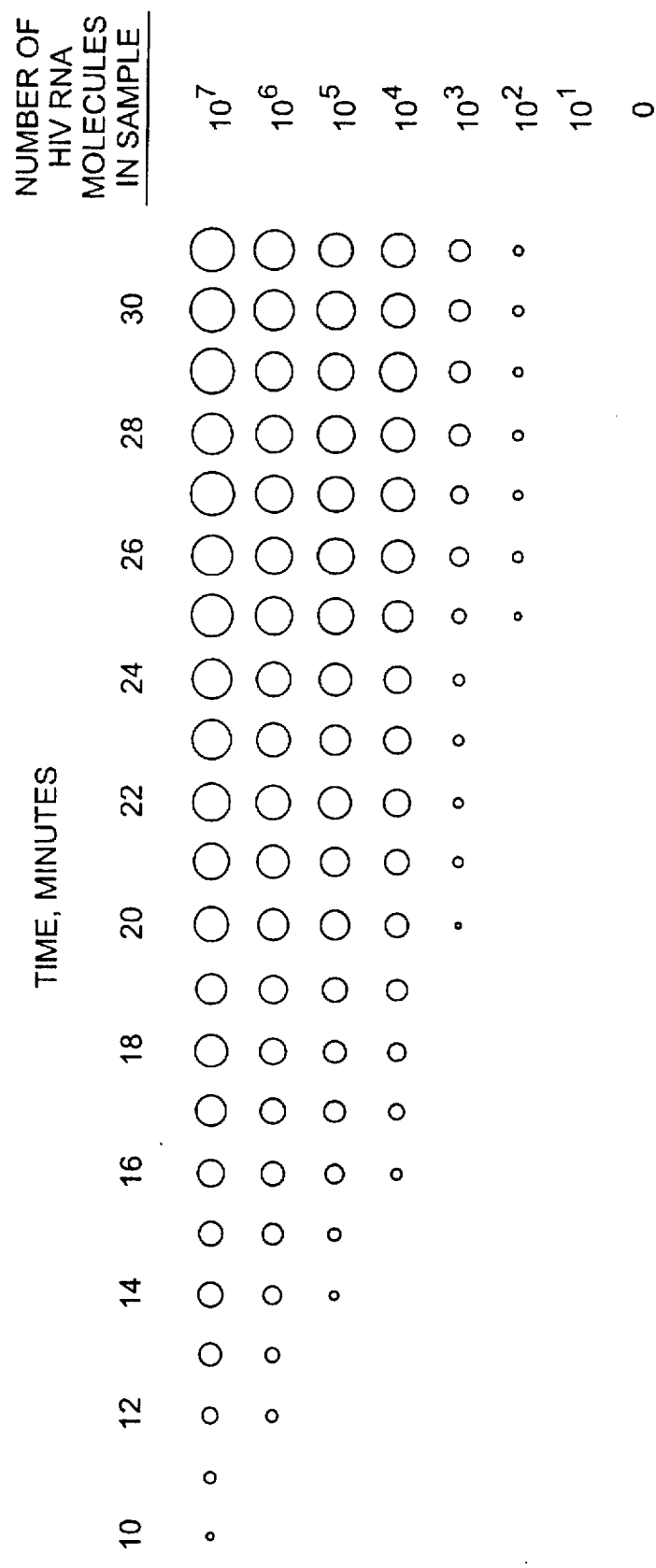
FIG. 4 shows typical results of an assay according to Example 1 for known amounts of target molecule.

D. Results The results demonstrate that it is possible to achieve very high sensitivity with no background. FIG. 4 shows a typical result of the assay described above for a dilution series of molecules of HIV integrase RNA. FIG. 4 is an autoradiogram. Each row depicts the signal from a given sample over time, as indicated. The intensity of each dot in FIG. 4 is proportional to the amount of RNA that was present in the tube at the time the sample was withdrawn. The time at which RNA can first be seen in the autoradiogram depended upon the number of targets that were present. The greater the number of targets, the earlier the signal appeared. There is a delay of at least about two-minutes for every 10-fold decrease in the number of targets. As few as a 100 targets molecules gave rise to a clear signal. Ten target molecules, or no target molecules, did not produce a signal, even after an additional eight minutes of incubation (not shown). One hundred molecules of HIV RNA target were clearly detectable; and anything less gave no signal at all.

As stated, the minimum number of targets that could be detected was a hundred molecules. However, the number of ligated replicatable RNA molecules in the corresponding tube prior to replication was considerably less. We have experimentally determined that the number of probe-target complexes remaining after hybridization, capture, washing, and release is 30 percent of the original number of targets present. Furthermore, we have determined that the efficiency of ligation was 10 percent. Therefore, in the tube that originally contained 100 target molecules, only 3 replicatable RNA molecules were likely to be present. Since at least 1 replicatable RNA molecule is required to initiate an amplification reaction, samples containing less than 100 molecules are unlikely to generate a signal. Since an infected clinical sample is likely to contain at least 1,000 target molecules (corresponding to a single infected cell), this extremely sensitive assay has adequate sensitivity for virtually all clinical applications. The improvement in synthesis of probe 9 reported above, which triples ligation efficiency, will improve the sensitivity of this assay even more.

Figure 5:
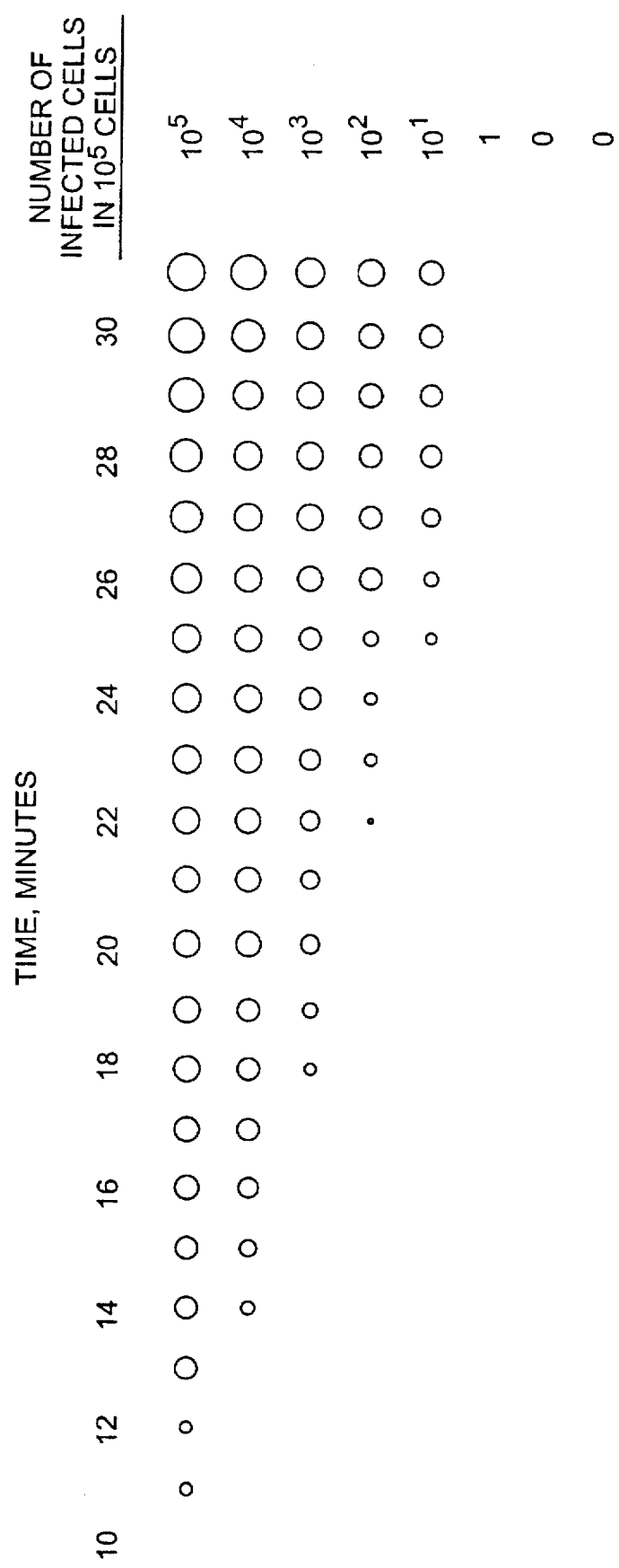
FIG. 5 shows the results of an assay according to Example 1 for known amounts of infected cells.
Figure 6:
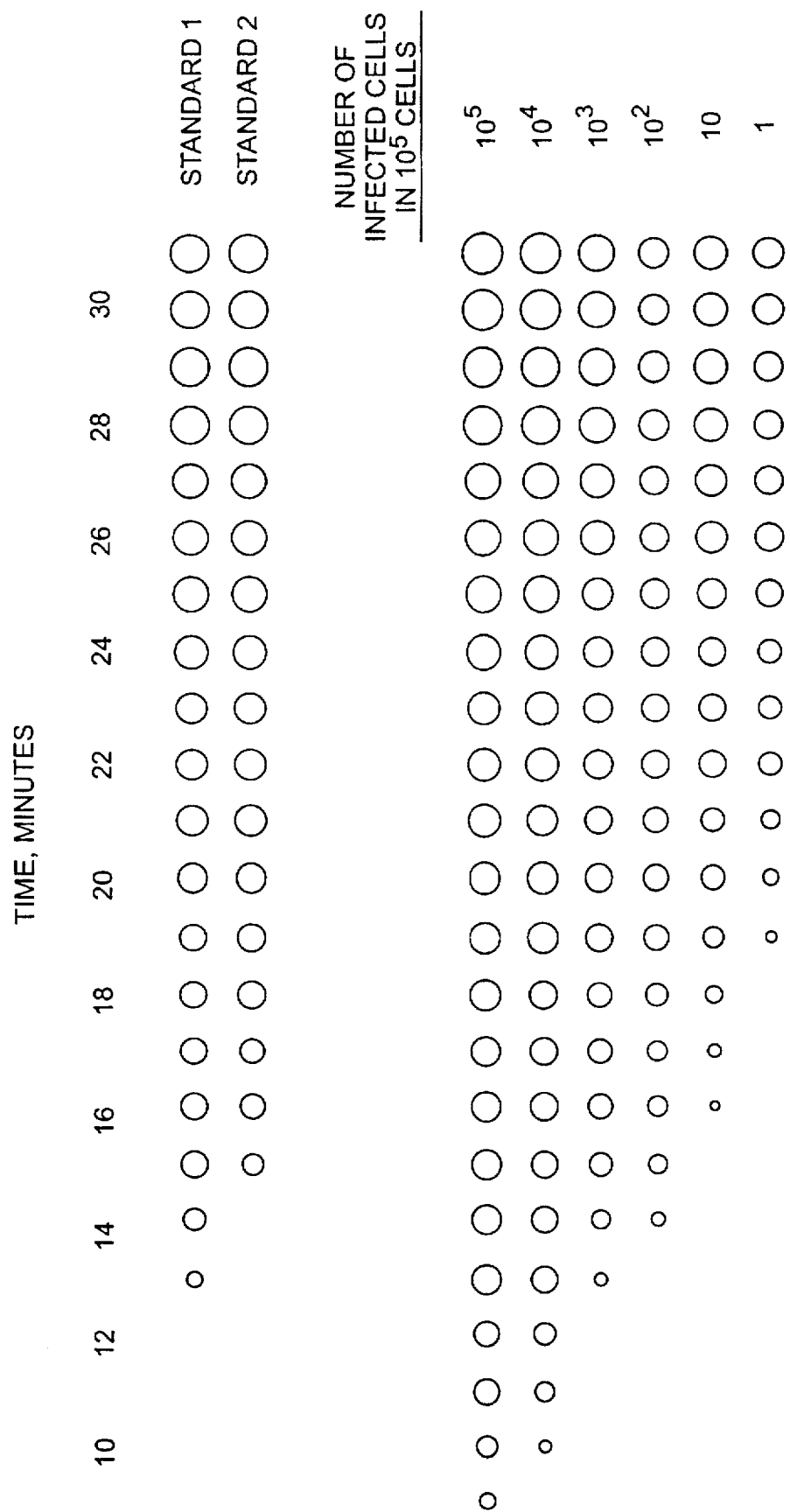
FIG. 6 shows the results of another assay according to Example 1 for known amounts of infected cells.

FIGS. 5 and 6 show the results of two experiments designed to demonstrate the clinical utility of this invention. They depict the results of assays according to this example on samples containing HIV-infected human peripheral lymphocytes. FIGS. 5 and 6 are autoradiograms as described in connection with Figure 4. The results of the two experiments, when considered together, show that one infected cell can be detected in a sample containing 100,000 uninfected cells, and that no signal is seen in samples that contain no infected cells. In both experiments each sample contained a total of 100,000 cells. In the first experiment (FIG. 5), the results show a clear relationship between the number of infected cells in a sample and the time of appearance of the signal. The greater the number of infected cells, the earlier the signal appeared. Thus, the assay is quantitative as well as qualitative. The two controls, each of which contained 100,000 uninfected cells (and no infected cells), produced no signal. However, the tube that contained one infected cell also did not give a signal. We hypothesized that, after lysis, the sample was not mixed completely. The lysed samples are extremely viscous (due to the presence of cellular DNA), and since there were only about six infected cells in the 240 microliter volume of the lysate, the probability of not sampling any HIV RNA in the 40 microliter sample withdrawn from the sample for the assay was high. In order to eliminate such a possibility, the samples were frozen and thawed and then exhaustively mixed, prior to using them in the next experiment. The assay was repeated with these well-mixed samples. The results, shown as the bottom six samples in FIG. 6, demonstrate that our hypothesis was correct and that, after proper mixing, the tube containing the nucleic acid from about one infected cell gave a strong signal with an appropriate delay time.

Another objective of the second experiment was to estimate the number of molecules of HIV RNA in each infected cell. We prepared two standards for this purpose. Standard 1, the first standard tube, contained 1,000,000 HIV integrase mRNA transcripts. Standard 2, the second standard tube contained a lysate from 100,000 uninfected cells and 1,000,000 molecules of HIV integrase mRNA transcripts. The results of the experiment, shown as the top two samples in FIG. 6, show that the presence of lysate from the uninfected cells has only a slight quenching effect. From the signal obtained from this internal standard, we were able to estimate that each infected cell contained about 3,000 HIV target molecules.

A note of caution is in order. Our laboratory is used for research on replicatable RNA molecules, which have a tendency to become airborne contaminants. In a test of the above assay, we obtained an aberrant signal in one of the tubes. Electrophoretic analysis of the amplified RNA revealed that it was not the reporter. Qβ replicase will amplify a number of RNAs, and our sample had become contaminated.

Example 2

DNA Target, DNA Binary Probes, RNA Capture Probes and RNase H Cleavage

Figure 7:
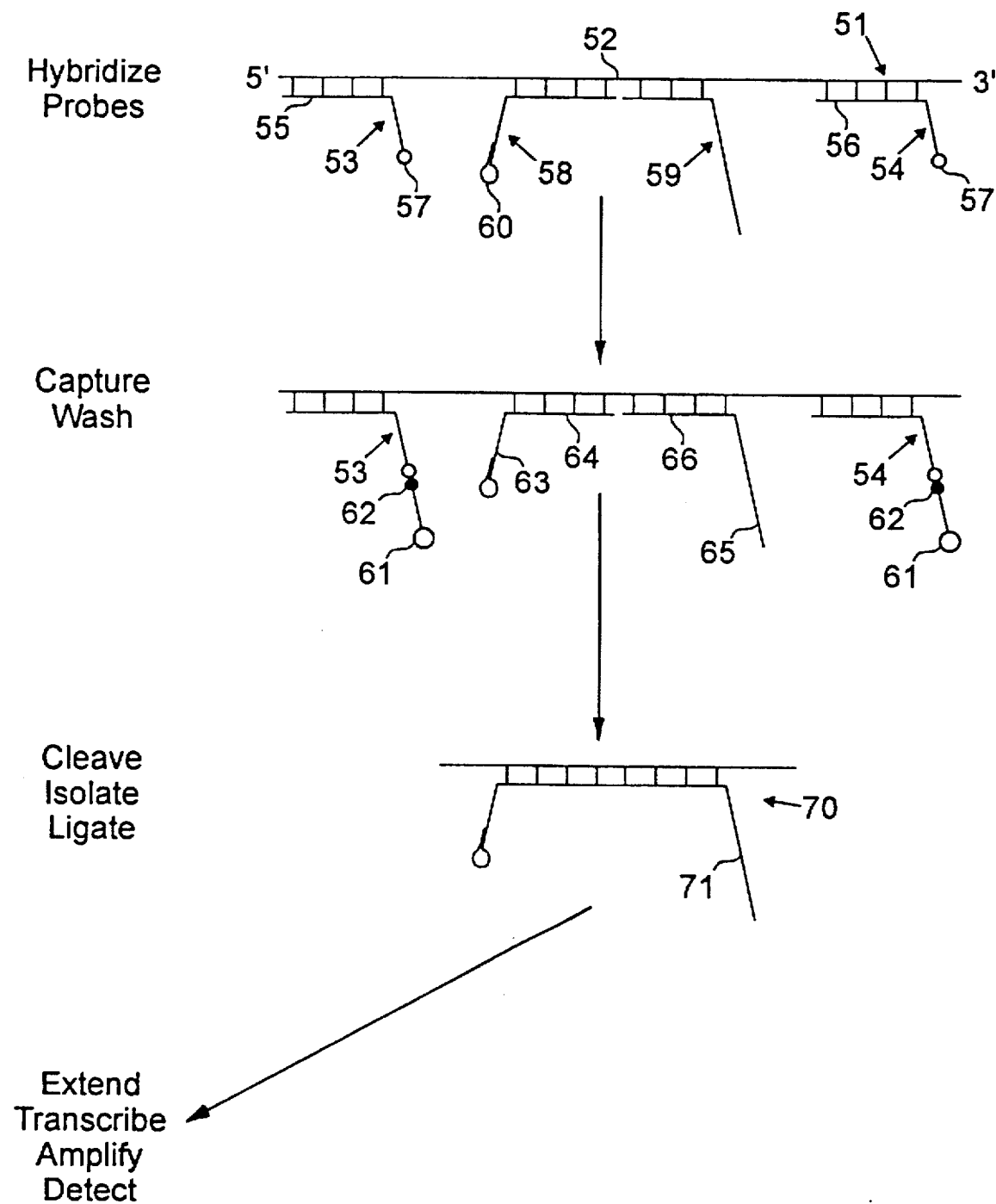
FIG. 7 depicts the assay of Example 2.

This preferred embodiment, depicted generally in FIG. 7, is for target DNA 51 and utilizes binary probes 58, 59 made of DNA. In this example, the capture probes 53, 54 are made of RNA, with a biotin moiety, in this case a terminal biotin moiety 57, for immobilization on a solid surface. The sequence of the capture probes is shown in FIG. 8. Each binary probe is a portion of a DNA template that can be transcribed into an amplifiable RNA. Binary probe 58 contains at its 5' end 64 twenty-two nucleotides that can hybridize to HIV RNA 51 in the region 4532–4553, part of target sequence 52. Adjacent to this probe sequence 64 are sixty nucleotides 63 that encode the 5' end of MDV-1(+) RNA. The 3' end of the probe 58 forms a hairpin structure 60. When the 3' end of this DNA is extended by incubation with the Klenow fragment of E. coli DNA polymerase, the resulting double-stranded DNA contains a promoter for T7 RNA polymerase directed towards the MDV-1 sequence. FIG. 8 shows the sequence of probe 58, including hairpin structure 60. Box 67 shows what will be the T7 promoter once the 3' end of probe 58 is extended to "fill the box" 67. Binary probe 59 contains at its 3' end 66 twenty-three nucleotides complementary to the region 4554–4576 of HIV RNA, part of target sequence 52. Adjacent to this probe sequence 66 is segment 65, that comprises 158 nucleotides that encode the 3' end of MDV-1(+) RNA. The sequence of the two DNA binary probes is shown in FIG. 8. Probe 58 was prepared by the ligation of two oligodeoxyribonucleotides prepared on a DNA synthesizer. Probe 59 can be similarly prepared. We prepared probe 59, however, by successively cloning DNA sequences into a bacteriophage M13 vector. Single-stranded DNA from the phage was isolated. This DNA was cleaved at the ends of the probe sequence by restriction endonucleases. The sites of cleavage were made double stranded by hybridization with oligodeoxyribonucleotides. The cleaved probe sequence was purified by gel electrophoresis.

These probes are hybridized to the HIV RNA, and the hybrids are captured, and washed in the same manner as described in Example 1. After washing, the paramagnetic particles are incubated with RNase H. RNase H degrades those capture probes that are hybridized to their targets, releasing the binary probes-target hybrids 70 (shown in FIG. 7) into the supernatant. The hybrids in the supernatant are then separated from the paramagnetic particles and transferred to a new test tube. The hybrids are then incubated with T4 DNA ligase, in order to link those binary probes that are correctly hybridized to their targets. After ligation, the hybrids are incubated with the Klenow fragment of E. coli DNA polymerase and T7 RNA polymerase in order to generate transcripts 71. These incubations are depicted as separate steps in FIG. 7, for illustration. The combined action of these enzymes leads to the synthesis of replicatable RNA molecules, which are subsequently amplified exponentially by incubation with Qβ replicase (as described in Example 1).

Example 3

RNA Target, RNA Binary Probes, DNA or RNA Capture Probe and Ribozyme Cleavage

Figure 9:
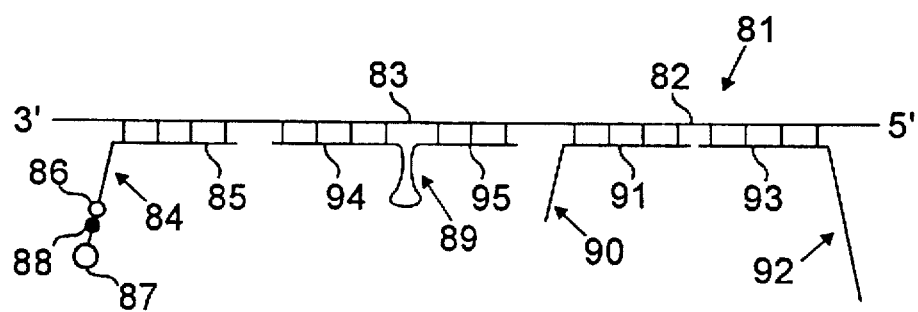
FIG. 9 depicts the assay of Example 3.

Our most preferred method of target-dependent release of reporter probe-target hybrids is cleavage of the targets by incubation with RNase H. In certain situations, a ribozyme may be used to cleave the target specifically in the region between the capture probe and the reporter probe or probes. Although we prefer a "hammerhead" ribozyme (Haseloff & Gerlach, 1988) for this cleavage, any other ribozyme which can be targeted towards this region can be used. FIG. 9 illustrates one embodiment of this example in which a hammerhead ribozyme is used.

Target RNA 81 contains target sequence 82. A single DNA capture probe 84, containing hybridization sequence 85 and biotin moiety 86 is shown attached to paramagnetic particle 87 via its streptavidin coating 88. A pair of RNA binary reporter probes 90, 92 are shown hybridized adjacent to one another on target sequence 82 via their respective sequences 91, 93. Hybridized to target 81 at a site between capture probe 84 and reporter probes 90, 92 is hammerhead ribozyme 89, that contains hybridization sequences 94, 95. Sequences 94, 95 are sometimes called "recognition sequences."

The ribozyme 89 is designed such that recognition sequence 94 (25–30 nucleotides in length) is longer than recognition sequence 95 (6–7 nucleotides in length). Ribozyme 89 is added as an additional probe. To effect cleavage of the target at 83, the magnesium ion concentration is adjusted to 20 millimolar, and the tubes are incubated for 60 minutes at 55° C. Since recognition sequence 95 is too small to hold the cleaved target, the reporter probes-target hybrids are released into the solution. This release is target-dependent. The release is followed by ligation of binary probes 90, 92 by incubation with T4 DNA ligase. Next, the ligated probes, i.e., the reporter molecule (not shown) is amplified by incubation with Qβ replicase.

In an alternative embodiment of this example, an RNA capture probe is used and the head of the capture probe is a ribozyme (or the head of the capture probe comprises a ribozyme and an additional sequence that is complementary to the target).

Example 4

RNA Target, DNA Binary Probes, DNA Capture Probe and RNase III Cleavage with the Use of an RNA Site-Identifying Probe The reporter probe-target hybrids can be released in a target-dependent manner with the aid of a 40–50 nucleotide-long site-identifying probe, which we sometimes call a "release probe." That probe should be made of RNA and can be hybridized to the RNA target along with the other probes. Incubation with RNase III cleaves the target between the capture probe and the binary reporter probes, releasing the binary probes-target hybrids into solution for amplification. RNase III cleavage sites have been described in the literature as specific sequences in double-stranded RNA, but we have observed that any double-stranded RNA more than 30 nucleotides long is a good substrate for RNase III. Because of this, a hybrid between an RNA reporter probe and an RNA target is degraded, and DNA reporter probes and DNA capture probes should be used.

Figure 10:
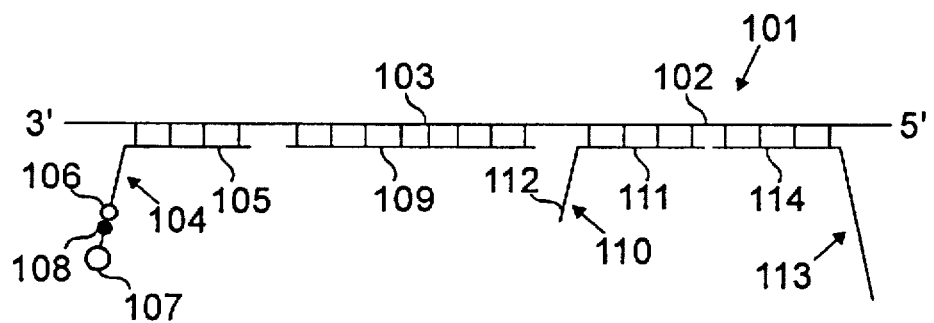
FIG. 10 depicts the assay of Example 4.

A preferred design for DNA binary probes is depicted in FIG. 10. Target RNA contains target sequence 102. A single DNA capture probe 104, containing hybridization sequence 105 and biotin moiety 106 is shown attached to paramagnetic particle 107 via its streptavidin coating 108. A pair of DNA binary reporter probes 110, 113 are shown hybridized adjacent to one another on target sequence 102 via their respective sequences 111, 114. Probe 110 includes terminal region 112 that can be extended to form a T7 promoter, similarly to probe 58 of Example 2. Site-identifying RNA probe 59 is shown hybridized to target 101 between the capture probe and the reporter probes. Probe 59 is as described above. Incubation with RNase III cleaves target 101 at 103.

We have demonstrated that DNA binary probes such as 110, 113 can be ligated by incubation with T4 DNA ligase in a target-dependent manner. Amplifiable reporter RNAs are generated by transcription of the ligated DNA binary probes by incubation with T7 RNA polymerase. Subsequent amplification of the reporter RNAs by incubation with Qβ replicase leads to a detectable signal. When the reporter molecule is a recombinant MDV-1 RNA, at least, the Klenow fragment of *E. coli* DNA polymerase is added (and, of course, deoxyribonucleotides are added) with the T7 RNA polymerase to complete the promoter, if necessary, and to further extend the DNA strand to form a double-stranded template.

Example 5
RNA Target, DNA Binary Probes, RNA Capture Probe and RNase III Cleavage Instead of the DNA capture probe described in Example 4, the capture probe can be made of RNA. This makes it unnecessary to use a site-identifying probe. The capture probe-target hybrids themselves are substrates for RNase III. Incubation with RNase III specifically releases the binary probes-target hybrids. This release is followed by incubation with T4 DNA ligase, T7 RNA polymerase (and possibly the Klenow fragment of *E. coli* DNA polymerase, as discussed in Example 4), and Qβ replicase, to generate an amplified signal.

Example 6
RNA Target, DNA Binary Probes, DNA Capture Probe and RNase A Cleavage If the capture probes and the reporter probes are made of DNA, then it is possible to use any single-strand-specific ribonuclease, such as RNase A, for release. RNase A does not cleave the target in the probe-target region, because its normal substrate is single-stranded RNA, but release is still specific, because target cleavage occurs between the capture probe and the target sequence. Nonspecifically bound reporter probes remain on the capture probes, which are permanently linked to the surface of the particles. Release is followed by incubation with T4 DNA ligase, T7 RNA polymerase (and possibly the Klenow fragment of *E. coli* DNA polymerase, as discussed in Example 4), and Qβ replicase, to generate an amplified signal.

Example 7
DNA Target, Unary or Binary Probes, DNA Capture Probe and Restriction Endonuclease Cleavage If the target is DNA, a restriction enzyme can be used. The sequence of the head of the capture probe is chosen such that it contains a restriction endonuclease recognition site. Reporter probe-target hybrids are released from the capture probes by incubating, e.g., the paramagnetic particles with an appropriate restriction endonuclease. The preferred embodiment of the reporter probe is a pair of RNA binary probes, as in Example 1, but the reporter probe can be a pair of DNA binary probes, as in Example 4, or the reporter probe could be a DNA or RNA unary probe. If binary probes are used, the released binary probes-target hybrids are then incubated with T4 DNA ligase and then amplified, directly or indirectly.

Example 8
DNA Target, DNA Binary Probes, RNA Capture Probe and RNase H Cleavage If the target and the reporter probes are DNA, while the capture probe is made of RNA, RNase H can be used to specifically release the binary probes-target hybrids from the capture probes. Release is followed by incubation with T4 DNA ligase, T7 RNA polymerase (and possibly the Klenow fragment of *E. coli* DNA polymerase, as discussed in Example 4), and Qβ replicase, to generate an amplified signal.

Example 9
Ribozyme Ligase

This example describes an assay for an RNA target using RNA binary probes and a "tethered" ribozyme ligase, which is an RNA molecule comprised of three regions: (1) a ribozyme ligase sequence; (2) a "holdfast", which is a sequence complementary to a region of the target that is near to the target sequence; and (3) a "tether", which is a sequence joining the ribozyme ligase sequence to the holdfast. Tethered ribozyme ligases are disclosed in Lizardi et al. Ser. No. 08/315,191, for Diagnostic Assays for RNA Using RNA Binary Probes, filed on the same date as this application, by Tyagi, Landegren, Lizardi, Kramer and Szostak. It utilizes Tetrahymena ribozyme ligase (Doudna and Szostak, 1989) and special binary probes as disclosed in Lizardi et al. Ser. No. 08/315,191.

A. Preparation of Binary Reporter Probes and a Tethered Ribozyme Ligase

The "first probe" is a 71 nucleotide-long RNA generated by in vitro transcription of an artificial gene. The sequence of this RNA is as follows:
5'-GGGGACCCCCCC- GGAAGGGGGGGACGAG-GUGCGGGCACCUCGUACGGGAGUUC-GAGCGUGAC <u>GACCGUAGU</u>-3'. The last 9 nucleotides of this RNA form a "first probe sequence"(underlined) that is complementary to the sequence 3'-UUGGCAUCG-5', which is part of the HIV-1 RNA target sequence.

The "second probe" is a 186-nucleotide-long RNA with the sequence:
5'-<u>GACUGGUGAAAUUGCUGCCAUUGUCUGUA</u>-GCACGCGCUAGCGCUUUCGCGCUCUCCCAGGUG ACGCCUCGUGAAGAGGCGCGACCU-UCGUGCGUUUCGGCAACGCACGAGAAC-CGCCACGCUGCUUC GCAGCGUGGCUCCUUCGCGCAGCCCGCUGCGCG-AGGUGACCCCCCGAAGGGGGGUUCCC-3'. The first nucleotide of this RNA is a guanosine, which does not pair to HIV-1 RNA, but is required for ligation by the Tetrahymena ribozyme ligase (Doudna & Szostak, 1989). The next 28 nucleotides form a "second probe sequence"(underlined) that is complementary to the sequence 3'-UGACCACUUUAACGACGGUAACAGACAU-5', which is the other part of the HIV-1 RNA target sequence adjacent to the 5' end of sequence 3'-UUGGCAUCG-5'.

The second probe is generated by in vitro transcription of an artificial gene that codes for the desired RNA sequence and contains a T7 promoter. The artificial gene is generated by the polymerase chain reaction (Erlich et al., 1991) using the following primers:
5'-TGCGTAATACGACTCACTATAGACTGGTGAAATT-GCTGCCATTGTCTGTAGCACGCTGCTAG CGCTTTCGCGCTCTCC-3' and 5' GGGGAACCCCCCT-TCGGGGGGTCACC 3'. These primers are used in a polymerase chain reaction in the presence of plasmid pT7MDVHIV20, described at page 1827 of Lomeli et al., 1989, to generate the artificial gene for the synthesis of the second probe. The 186-nucleotide-long transcript is purified by polyacrylamide gel electrophoresis.

The tethered ribozyme ligase is generated by in vitro transcription, as described by Doudna & Szostak (1989). An artificial gene for the transcription of the tethered ribozyme ligase is generated by PCR from plasmid pJD1100 (Doudna & Szostak, 1989) using the following primers:

5'-GCGTAATACGACTCACTATAGGGTTTTTACTGGC-CATCTTCCTGCTAATTTTAAGTTGAGAG TTATCAGGCATGCACCTG-3' and 5'-CTAGCTCCCATTAAGGAGAG-3'. The product of in vitro transcription is 345 nucleotides long and contains a holdfast having the sequence 5'-GTTTTTACTGGCCATCTTCCTGCTAATTTTAA-3' and a tether having the sequence 5'-TTTGAG-3', which is connected to the P2 stem of the Tetrahymena ribozyme ligase (Doudna & Szostak, 1989). The holdfast is complementary to a sequence in HIV-1 RNA that is five nucleotides removed from the target sequence.

Each binary probe was tested to see if it could be exponentially replicated by incubation with Qβ replicase, and neither was.

B. Assay for HIV-1 RNA

The assay is the same as the assay of Example 1, except that each sample is dissolved in 20 microliters of 5M GuSCN; then to each sample is added an 80-microliter solution containing: $10^{13}$ molecules of each capture probe, $2 \times 10^{10}$ molecules of first probe, $2 \times 10^{10}$ molecules of second probe, and $2 \times 10^{10}$ molecules of tethered ribozyme ligase. Hybridization and washing are carried out in 1M GuSCN, instead of 2M GuSCN. Then, instead of washing with 1× ligase buffer, ribozyme ligase buffer (10 mM $NH_4Cl$, 20 mM $MgCl_2$, 4 mM spermidine, and 30 mM Tris-HCl, pH 7.4) is used. One unit of RNase H, dissolved in ribozyme ligase buffer is then added, and the binary probes-target hybrids are released from the surface of the paramagnetic particles by a 10-minute incubation at 37° C. The binary probes-target hybrids are then isolated from the particles, as described in Example 1. The isolated binary probes-target hybrids are then incubated for 60 minutes at 58° C. (Doudna & Szostak, 1989) to ligate the binary probes in a target-directed fashion. The remainder of the assay is as described in Example 1.

References

Barany, F. (1991) Genetic Disease Detection and DNA Amplification Using Cloned Thermostable Ligase. Proc. Natl. Acad. Sci. U.S.A. 88, 189–193.

Chu, B. C. F., Kramer, F. R., and Orgel, L. E. (1986) Synthesis of an Amplifiable Reporter RNA for Bioassays. Nucleic Acids Res. 14, 5591–5603.

Doudna, I. A. and Szostak, J. W. (1989) RNA-Catalyzed Synthesis of Complementary-Strand RNA. Nature 339, 519–522.

Dunn, A. R., and Hassell, J. A. (1977) A Novel Method to Map Transcripts: Evidence for Homology between an Adenovirus mRNA and Discrete Multiple Regions of the Viral Genome. Cell 12, 23–36.

Erlich, H. A., Gelfand, D. and Sninsky, J. J. (1991) Recent Advances in the Polymerase Chain Reaction. Science 252, 1643–1651.

Gillespie, D., and Spiegelman, S. (1965) A Quantitative Assay for DNA-RNA Hybrids with DNA Immobilized on a Membrane. J. Mol. Biol. 12, 829–842.

Guatelli, J. C., Whitfield, K. M., Kwoh, D. Y., Barringer, K. J., Richman, D. D., and Gingeras, T. R. (1990) Isothermal, in vitro Amplification of Nucleic Acids by a Multienzyme Reaction Modeled after Retroviral Replication. Proc. Natl. Acad. Sci. U.S.A. 87, 1874–1878.

Haseloff, J., and Gerlach, W. L. (1988) Simple RNA Enzymes with New and Highly Specific Endoribonuclease Activities. Nature 334, 585–591.

Hunsaker, W. R., Badri, H., Lombardo, M., and Collins, M. L. (1989) Nucleic Acid Hybridization Assays Employing dA-Tailed Capture Probes. II. Advanced Multiple Capture Methods. Anal. Biochem. 181, 360–370.

Konarska, M. M. and Sharp, P. A. (1989) Replication of RNA by the DNA-Dependent RNA Polymerase of Phage T7. Cell 57, 423–431.

Kramer, F.R., and Lizardi, P.M. (1989) Replicatable RNA Reporters. Nature 339, 402–403.

Krinke, L., and Wulff, D. L. (1990) The Cleavage Specificity of RNase III. Nucleic Acids Res. 18, 4809–4815.

Landegren, U., Kaiser, R., Sanders, J., and Hood, L. (1988) A Ligase-mediated Gene Detection Technique. Science 241, 1077–1080.

Landegren, U. and Hood, L. (1991) Method of Detecting a Nucleotide Change in Nucleic Acids. U.S. Pat. No. 4,988,617.

Leary, J. J., Brigati, D. J., and Ward, D. C. (1983) Rapid and Sensitive Colorimetric Method for Visualizing Biotin-labeled DNA Probes Hybridized to DNA or RNA Immobilized on Nitrocellulose: Bio-blots. Proc. Natl. Acad. Sci. U.S.A. 80, 4045–4049.

Levisohn, R. and Spiegelman, S. (1968) Proc. Natl. Acad. Sci. U.S.A. 60, 866–892.

Lizardi, P., Guerra, C. E., Lomeli, H., Tussie-Luna, I., and Kramer, F. R. (1988) Exponential Amplification of Recombinant-RNA Hybridization Probes. Biotechnology 6, 1197–1202.

Lizardi, P. M., Kramer, F. R., Tyagi, S., Guerra, C. E., and Lomeli-Buyoli, H. M. (1992) Nucleic Acid Probes Containing an Improved Molecular Switch. U.S. Pat. No. 5,118,801.

Lomeli, H., Tyagi, S., Pritchard, C. G., Lizardi, P. M., and Kramer, F. R. (1989) Quantitative Assays Based on the Use of Replicatable Hybridization Probes. Clin. Chem. 35, 1826–1831.

Martinelli, R. M., Donahue, J. J., and Unger, J. T. (1992) Amplification of Midivariant DNA Templates. European Patent Application Publication No. 0 481 704 Al.

Morrissey, D. V., Lombardo, M., Eldredge, J. K., Kearney, K. R., Goody, E. P., and Collins, M. L. (1989) Nucleic Acid Hybridization Assays Employing dA-Tailed Capture Probes: I. Multiple Capture Methods. Anal. Biochem. 81, 345–359.

Pritchard, C. G. and Stefano, J. E. (1991) Detection of Viral Nucleic Acids by Qβ Replicase Amplification. Medical Virology 10 (de la Maza, L. M., and Peterson, E. M. eds), pp. 67–80, Plenum Press, New York.

Ranki, M., Palva, A., Virtanen, M., Laaksonen, M., and Soderlund, H. (1983) Sandwich Hybridization as a Convenient Method for Detection of Nucleic Acids in Crude Samples. Gene 21, 77–85.

Syvanen, A.-C., Laaksonen, M. and Soderlund, H. (1986) Fast Quantification of Nucleic Acid Hybrids by Affinity-based Hybrid Collection. Nucleic Acids Res. 14, 5037–5048.

Thompson, J., Solomon, R., Pellegrino, M., Sakai, K., Lewin, M., Feild, M., Castrovinci, M., Sacramone, L., and Gillespie, D. (1989) A Noise-free Molecular Hybridization Procedure for Measuring RNA in Cell Lysates. Anal. Biochem. 181, 371–378.

Walker, G. T., Fraiser, M. S., Schram, J. L., Little, M. C., Nadeau, J. G., and Malinowski, D. P. (1992) Strand Dis placement Amplification--an Isothermal, in vitro DNA Amplification Technique. Nucleic Acids Res. 20, 1691-1696.

Yabusaki, K. K., Isaacs, S. T., and Gamper, Jr., H. B. (1986) Nucleic Acid Hybridization Assay Employing Probes Crosslinkable to Target Sequences. U.S. Pat. No. 4,599,303.

---

We claim:

1. A nucleic acid sandwich hybridization assay to detect the presence in a sample of a preselected nucleic acid target selected from the group consisting of DNA and RNA and containing a target sequence comprising the steps of:

a) incubating the sample with at least one capture probe under conditions promoting hybridization of the at least one capture probe to said target, b) incubating the sample with a binary reporter probe that is not a capture probe under conditions promoting hybridization of the binary reporter probe to said target sequence, c) providing a support having a surface, d) immobilizing the at least one capture probe on said surface, e) washing said surface after completion of steps a through d, f) incubating the washed surface with ribonuclease H to cleave immobilized capture probe-target-reporter probes hybrids in a sequence-independent fashion at the capture probe-target hybrid to release binary reporter probe-target hybrids, g) separating the liquid from the surface after step f, h) ligating said binary reporter probe in the separated liquid from step g in a target-dependent fashion to form a reporter molecule, i) amplifying said reporter molecule in a reaction selected from the group consisting of ligase chain reaction, polymerase chain reaction, self-sustained sequence reaction, strand displacement amplification, RNA-directed RNA polymerization and target-dependent replication to form an amplified product, and j) detecting for the presence of said amplified product as an indication of the presence or absence of the preselected target in the sample, wherein the target sequence and the binary probe are one member of the group consisting of DNA and RNA and the at least one capture probe is the other member of the group consisting of DNA and RNA.

2. The assay according to claim 1, wherein said step of detecting is quantitative.

3. The assay according to claim 1, wherein the incubations of steps a and b are performed simultaneously, prior to the performance of step d.

4. The assay according to claim 1, wherein said binary reporter probe is a DNA probe and wherein the step of amplifying comprises transcribing said reporter molecule to produce an RNA transcript that is a template for an RNA-directed RNA polymerase and exponentially amplifying said transcript using an RNA-directed RNA polymerase.

5. The assay according to claim 1, wherein said binary reporter probe is an RNA template for Qβ replicase, and said step of ligating includes ligating with T4 DNA ligase.

6. The assay according to claim 1, wherein said at least one capture probe comprises two capture probes.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Human immunodeficiency virus type 1

( x i ) SEQUENCE DESCRIPTION: SEQ ID NO:1:

```
TACGACTGCT ACCAAGATAA CTTTTCCTTC TAAATGTGTA CAATCTAGC      49
```

( 2 ) INFORMATION FOR SEQ ID NO:2:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Human immunodeficiency virus type 1

( x i ) SEQUENCE DESCRIPTION: SEQ ID NO:2:

```
TACGATGTCT GTTGCTATTA TGTCTACTAT TCTTTCCCCT GCACTGTAC      49
```

( 2 ) INFORMATION FOR SEQ ID NO:3:

( i ) SEQUENCE CHARACTERISTICS:
        ( A ) LENGTH: 185 base pairs
        ( B ) TYPE: nucleic acid
        ( C ) STRANDEDNESS: single
        ( D ) TOPOLOGY: linear ( i i ) MOLECULE TYPE: RNA (genomic)

( v i ) ORIGINAL SOURCE:
        ( A ) ORGANISM: Human immunodeficiency virus type 1

( x i ) SEQUENCE DESCRIPTION: SEQ ID NO:3:

```
GGUGAAAUUG CUGCCAUUGA GAUCUAGAGC ACGGGCUAGC GCUUUCGCGC UCUCCCAGGU      60
GACGCCUCGU GAAGAGGCGC GACCUUCGUG CGUUUCGGUG ACGACGAGA  ACCGCCACGC     120
UGCUUCGCAG CGUGGCUCCU UCGCGCAGCC CGCUGCGCGA GGUGACCCCC CGAAGGGGGG     180
UUCCC                                                                185
```

( 2 ) INFORMATION FOR SEQ ID NO:4:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( i i ) MOLECULE TYPE: RNA (genomic)

( v i ) ORIGINAL SOURCE:
            ( A ) ORGANISM: Human immunodeficiency virus type 1

( x i ) SEQUENCE DESCRIPTION: SEQ ID NO:4:

GGGGACCCCC CCGGAAGGGG GGGACGAGGU GCGGGCACCU CGUACGGGAG UUCGACCGUG    60

ACGCUCUAGC AGGCGGCCUU AACUGUAGUA CU    92

( 2 ) INFORMATION FOR SEQ ID NO:5:

( i ) SEQUENCE CHARACTERISTICS:
            ( A ) LENGTH: 49 base pairs
            ( B ) TYPE: nucleic acid
            ( C ) STRANDEDNESS: single
            ( D ) TOPOLOGY: linear ( i i ) MOLECULE TYPE: RNA (genomic)

( v i ) ORIGINAL SOURCE:
            ( A ) ORGANISM: Human immunodeficiency virus type 1

( x i ) SEQUENCE DESCRIPTION: SEQ ID NO:5:

GGCGACUGCU ACCAAGAUAA CUUUUCCUUC UAAAUGUGUA CAAUCUAGC    49

( 2 ) INFORMATION FOR SEQ ID NO:6:

( i ) SEQUENCE CHARACTERISTICS:
            ( A ) LENGTH: 49 base pairs
            ( B ) TYPE: nucleic acid
            ( C ) STRANDEDNESS: single
            ( D ) TOPOLOGY: linear ( i i ) MOLECULE TYPE: RNA (genomic)

( v i ) ORIGINAL SOURCE:
            ( A ) ORGANISM: Human immunodeficiency virus type 1

( x i ) SEQUENCE DESCRIPTION: SEQ ID NO:6:

GGCGAUGUCU GUUGCUAUUA UGUCUACUAU UCUUUCCCCU GCACUGUAC    49

( 2 ) INFORMATION FOR SEQ ID NO:7:

( i ) SEQUENCE CHARACTERISTICS:
            ( A ) LENGTH: 135 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Human immunodeficiency virus type 1

( i x ) FEATURE:
            ( A ) NAME/KEY: stem_loop
            ( B ) LOCATION: 113..117

( x i ) SEQUENCE DESCRIPTION: SEQ ID NO:7:

CCATCTTCCT GCTAATTTTA AGTCACGGTC GAACTCCCGT ACGAGGTGCC CGCACCTCGT    60

CCCCCCCTTC CGGGGGGGTC CCCTATAGTG AGTCGTATTA GTCGAGATAA CGGTGGGCGT    120

TATCTCGACT AATAC    135

( 2 ) INFORMATION FOR SEQ ID NO:8:

( i ) SEQUENCE CHARACTERISTICS:
            ( A ) LENGTH: 181 base pairs
            ( B ) TYPE: nucleic acid (C) STRANDEDNESS: single
(D) TOPOLOGY: linear (ii) MOLECULE TYPE: DNA (genomic)

(vi) ORIGINAL SOURCE:
(A) ORGANISM: Human immunodeficiency virus type 1

(xi) SEQUENCE DESCRIPTION: SEQ ID NO:8:

```
GGGAACCCCC CTTCGGGGGG TCACCTCGCG CAGCGGGCTG CGCGAAGGAG CCACGCTGCG      60
AAGCAGCGTG GCGGTTCTCG TGCGTCACCG AAACGCACGA AGGTCGCGCC TCTTCACGAG     120
GCGTCACCTG GGAGAGCGCG AAAGCGCTAG CCCGTGACTC TGTATGAACT GTTTTACTG     180
G                                                                    181
```

(2) INFORMATION FOR SEQ ID NO:9:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Human immunodeficiency virus type 1

(xi) SEQUENCE DESCRIPTION: SEQ ID NO:9:

```
GGGGACCCCC CCGGAAGGGG GGGACGAGGU GCGGGCACCU CGUACGGGAG UUCGAGCGUG      60
ACGACCGUAG U                                                          71
```

(2) INFORMATION FOR SEQ ID NO:10:

(i) SEQUENCE CHARACTERISTICS:
(A) LENGTH: 186 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Human immunodeficiency virus type 1

(xi) SEQUENCE DESCRIPTION: SEQ ID NO:10:

```
GACUGGUGAA AUUGCUGCCA UUGUCUGUAG CACGCGCUAG CGCUUUCGCG CUCUCCCAGG      60
UGACGCCUCG UGAAGAGGCG CGACCUUCGU GCGUUUCGGC AACGCACGAG AACCGCCACG     120
CUGCUUCGCA GCGUGGCUCC UUCGCGCAGC CCGCUGCGCG AGGUGACCCC CCGAAGGGGG     180
GUUCCC                                                                186
```

(2) INFORMATION FOR SEQ ID NO:11:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Human immunodeficiency virus type 1

(xi) SEQUENCE DESCRIPTION: SEQ ID NO:11:

```
UACAGACAAU GGCAGCAAUU UCACCAGU                                         28
```

( 2 ) INFORMATION FOR SEQ ID NO:12:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: RNA (genomic)

( v i ) ORIGINAL SOURCE:
        ( A ) ORGANISM: Human immunodeficiency virus type 1

( x i ) SEQUENCE DESCRIPTION: SEQ ID NO:12:

```
GCUACGGUU                                                                          9
```

( 2 ) INFORMATION FOR SEQ ID NO:13:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Human immunodeficiency virus type 1

( x i ) SEQUENCE DESCRIPTION: SEQ ID NO:13:

```
TGCGTAATAC GACTCACTAT AGACTGGTGA AATTGCTGCC ATTGTCTGTA GCACGCTGCT        60

AGCGCTTTCG CGCTCTCC                                                     78
```

( 2 ) INFORMATION FOR SEQ ID NO:14:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
GCGTAATACG ACTCACTATA GGGTTTTTAC TGGCCATCTT CCTGCTAATT TTAAGTTGAG        60

AGTTATCAGG CATGCACCTG                                                   80
```

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
CTAGCTCCCA TTAAGGAGAG                                                   20
```

( 2 ) INFORMATION FOR SEQ ID NO:16:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GTTTTTACTG GCCATCTTCC TGCTAATTTT AA    32

( 2 ) INFORMATION FOR SEQ ID NO:17:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:17:

TTTGAG    6

( 2 ) INFORMATION FOR SEQ ID NO:18:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Human immunodeficiency virus type 1

( x i ) SEQUENCE DESCRIPTION: SEQ ID NO:18:

GGGGAACCCC CCTTCGGGGG GTCACC    26

( 2 ) INFORMATION FOR SEQ ID NO:19:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: RNA (genomic)

( v i ) ORIGINAL SOURCE:
    ( A ) ORGANISM: Human immunodeficiency virus type 1

( x i ) SEQUENCE DESCRIPTION: SEQ ID NO:19:

GCUACGGUU    9